(12) United States Patent
Brincat et al.

(10) Patent No.: US 9,483,618 B2
(45) Date of Patent: Nov. 1, 2016

(54) SYSTEMS, METHODS AND COMPUTER PROGRAM PRODUCTS FOR PROVIDING DISEASE AND/OR CONDITION SPECIFIC ADAPTIVE MOBILE HEALTH CONTENT, APPLICATIONS AND/OR SOLUTIONS

(71) Applicant: Exco InTouch, Sawbridgeworth (GB)

(72) Inventors: Mark Brincat, Kent (GB); Michael Hansen, Apex, NC (US); Madhav Vattikuti, Cary, NC (US)

(73) Assignee: Exco InTouch Limited, Herts (GB)

( * ) Notice: Subject to any disclaimer, the term of this patent is extended or adjusted under 35 U.S.C. 154(b) by 252 days.

(21) Appl. No.: 13/838,698

(22) Filed: Mar. 15, 2013

(65) Prior Publication Data

US 2013/0346090 A1 Dec. 26, 2013

Related U.S. Application Data

(60) Provisional application No. 61/663,034, filed on Jun. 22, 2012.

(51) Int. Cl.
*G06Q 50/22* (2012.01)
*G06Q 50/24* (2012.01)
*G06F 19/00* (2011.01)

(52) U.S. Cl.
CPC ......... *G06F 19/3418* (2013.01); *G06F 19/345* (2013.01)

(58) Field of Classification Search
CPC .... G06Q 50/22; G06Q 50/24; G06F 19/325; G06F 8/60; G06F 11/1433; G06F 19/3412
See application file for complete search history.

(56) References Cited

U.S. PATENT DOCUMENTS

| | | | |
|---|---|---|---|
| 5,722,418 A * | 3/1998 | Bro | G06F 19/3456 128/905 |
| 6,095,985 A | 8/2000 | Raymond et al. | |
| 2005/0055242 A1* | 3/2005 | Bello et al. | 705/2 |
| 2007/0129967 A1* | 6/2007 | Thompson | G06F 19/3443 705/2 |
| 2011/0184250 A1* | 7/2011 | Schmidt | G06Q 10/00 600/300 |
| 2013/0085798 A1* | 4/2013 | Spatola | G06Q 10/06 705/7.24 |

* cited by examiner

*Primary Examiner* — Joseph Burgess
(74) *Attorney, Agent, or Firm* — Myers Bigel & Sibley, P.A.

(57) ABSTRACT

Systems, methods and computer program products for providing condition specific adaptive content include receiving condition specific information into a data repository, defining requirements corresponding to the condition specific information, building a condition specific application based on the requirements, configuring the condition specific application corresponding to user-specific attribute and delivering the condition specific application to a processing device that is operable to execute the condition specific application.

10 Claims, 12 Drawing Sheets

SYSTEMS, METHODS AND COMPUTER PROGRAM PRODUCTS FOR PROVIDING DISEASE AND/OR CONDITION SPECIFIC ADAPTIVE MOBILE HEALTH CONTENT, APPLICATIONS AND/OR SOLUTIONS

CROSS-REFERENCE TO RELATED APPLICATION

This non-provisional patent application claims priority to provisional patent application No. 61/663,034 filed on Jun. 29, 2012 in the U.S.P.T.O, the contents of which in its entirety are herein incorporated by reference.

FIELD OF THE INVENTION

The present invention relates generally to communication and, more particularly, to systems, methods and computer program products for delivery of applications.

BACKGROUND

Many industries may utilize and/or rely on communications with multiple classes of users. For example, the healthcare and pharmaceutical industries may rely on communications between various classes including healthcare providers, such as doctors and/or nurses, patients, prospective patients, and/or clients, such as, for example, healthcare research organizations, medical device manufacturers and/or pharmaceutical companies, among others. Advances in technology have provided for wireless communication systems using, for example, mobile terminals. However, functionality of mobile terminals may vary as a function of hardware, software, and/or services, among others. Accordingly, currently available systems and methods may not be suitable for providing ubiquitous mobile applications through the various mobile terminals.

SUMMARY

Some embodiments of the present invention are directed to methods of providing condition specific adaptive content. Such methods may include receiving condition specific information into a data repository, defining condition specific application requirements corresponding to the condition specific information, building a condition specific application based on the requirements, configuring the condition specific application corresponding to user-specific attributes and delivering the condition specific application to a processing device that is operable to execute the condition specific application.

Some embodiments provide that the processing device includes a mobile terminal. In some embodiments, receiving the condition specific information includes receiving health condition related data. Some embodiments provide that receiving the condition specific information includes receiving disease specific data. Some embodiments provide that defining requirements corresponding to the condition specific information includes selecting a disease, selecting at least one disease attribute of multiple disease attributes, and selecting at least one disease functional component of the condition specific application corresponding to the selected at least one disease attribute.

In some embodiments, building the condition specific application includes defining function metadata corresponding to at least one functional component of the condition specific application, defining at least one function element based on the function metadata and defining a function interface that corresponds to the at least one functional component of the condition specific application.

Some embodiments provide that configuring the condition specific application corresponding to user-specific attributes includes defining general rules and/or workflow corresponding to the condition specific application, configuring multiple condition stages that are specific to the condition, mapping multiple behavior stages of the user that correspond to ones of the condition stages, mapping knowledge-base content to the condition stages and/or the behavior stages.

In some embodiments, delivering the condition specific application to the processing device that is operable to execute the condition specific application includes assessing multiple capabilities corresponding to the processing device, the user and/or at least one peripheral device attached thereto, packaging the condition specific application corresponding to the capabilities of the processing device, the user and/or at least one peripheral device and modifying the packaged condition specific application to include user specific data.

Some embodiments further include modifying at least one component and/or operating mode of the condition specific application responsive to a change in the condition and/or user behavior.

Some embodiments of the present invention include computer program products for providing condition specific adaptive content. The computer program products may include a non-transitory computer-readable medium having executable computer-readable program code therein, the computer-readable program code being configured to implement operations and/or methods disclosed herein.

Some embodiments are directed to computer program products that include a non-transitory computer readable storage medium having computer readable program code embodied therein. The computer readable program code may include computer readable program code that is configured to define requirements corresponding to disease specific information, computer readable program code that is configured to generate a disease specific application for execution on a mobile terminal, the disease specific application including functional elements corresponding to the disease and that is configured according to a stage of the disease and a corresponding patient behavioral stage, and computer readable program code that is configured to deliver the disease specific application to the mobile terminal based on properties corresponding to the mobile terminal.

Some embodiments are directed to computer systems. Such systems may include at least one processor and at least one memory coupled to the at least one processor, the memory including computer readable program code embodied therein that, when executed by the processor, causes the processor to perform operations as described herein.

It is noted that aspects of the inventive concept described with respect to one embodiment, may be incorporated in a different embodiment although not specifically described relative thereto. That is, all embodiments and/or features of any embodiment can be combined in any way and/or combination. These and other objects and/or aspects of the present inventive concept are explained in detail in the specification set forth below.

BRIEF DESCRIPTION OF THE DRAWINGS

The accompanying figures are included to provide a further understanding of the present inventive concept, and are incorporated in and constitute a part of this specification. The drawings illustrate some embodiments of the present inventive concept and, together with the description, serve to explain principles of the present inventive concept.

DETAILED DESCRIPTION

Figure 1:
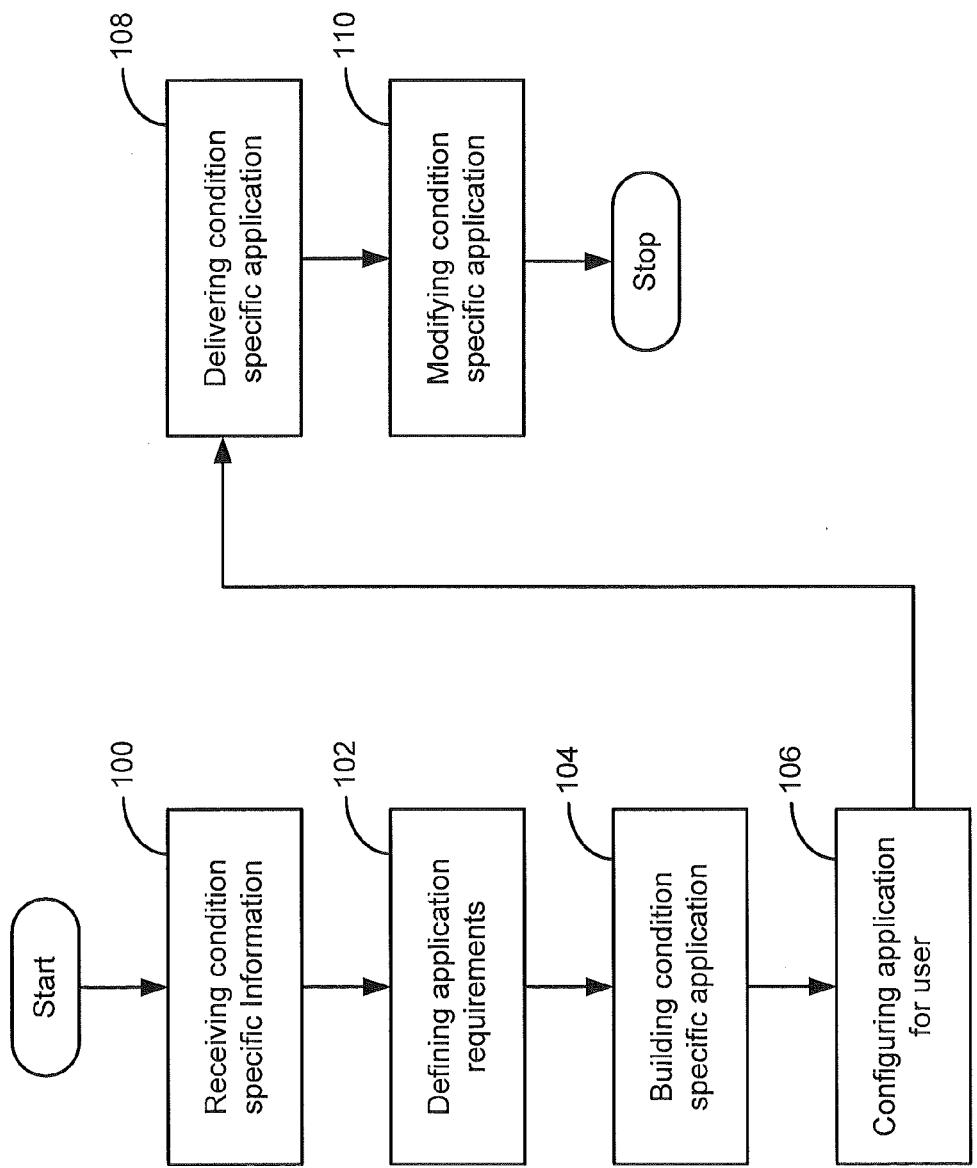
FIG. 1 is a block diagram illustrating operations for providing condition specific adaptive content according to some embodiments of the present invention.

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present invention. In addition, as used herein, the singular forms "a", "an" and "the" are intended to include the plural forms as well, unless the context clearly indicates otherwise. It also will be understood that, as used herein, the term "comprising" or "comprises" is open-ended, and includes one or more stated elements, steps and/or functions without precluding one or more unstated elements, steps and/or functions. The term "and/or" includes any and all combinations of one or more of the associated listed items.

It will also be understood that when an element is referred to as being "connected" to another element, it can be directly connected to the other element or intervening elements may be present. In contrast, when an element is referred to as being "directly connected" to another element, there are no intervening elements present. It will also be understood that the sizes and relative orientations of the illustrated elements are not shown to scale, and in some instances they have been exaggerated for purposes of explanation.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein. The present invention will now be described more fully hereinafter with reference to the accompanying drawings, in which some embodiments of the invention are shown. This invention, however, may be embodied in many different forms and should not be construed as limited to the embodiments set forth herein. Rather, these embodiments are provided so that this disclosure will be thorough and complete, and will fully convey the scope of the invention to those skilled in the art.

It should be construed that forgoing general illustrations and following detailed descriptions are exemplified and an additional explanation of claimed inventions is provided.

Reference numerals are indicated in detail in some embodiments of the present invention, and their examples are represented in reference drawings. Throughout the drawings, like reference numerals are used for referring to the same or similar elements in the description and drawings.

Pursuant to embodiments of the present invention, systems and methods are provided for providing compliant messaging services. Compliance may be required for applications used in, for example, healthcare and/or pharmaceutical industries. In some embodiments, a sponsor, such as a pharmaceutical provider, for example, may initiate and/or manage a campaign such as, for example, a clinical and/or marketing study regarding a new drug and/or drug application and/or disease condition. In some embodiments, a campaign may include a prescription reminder service, health surveys and/or questionnaires, and/or services for increasing the patient's compliance with a clinical study or drug regimen. In this regard, a campaign may include a series of events and/or operations undertaken to achieve a specific goal. As described herein, campaigns may be directed to gathering and/or disseminating information and/or data corresponding to a clinical and/or marketing study regarding a new drug and/or drug application, disease condition and/or a prescription reminder service, among others. Concomitant with such studies may be strict requirements including audit trails, validation, authentication and/or confidentiality, among others. Additionally, as a practical matter, global connectivity, sufficient encryption and performance, multi-lingual capability and/or integration flexibility may be necessary as well. In this regard, a trusted third party to manage the management, data, communications, and/or compliance issues associated with such campaigns may be beneficial. For example, in some regulatory environments, sponsors may be prohibited from having direct contact with and/or storing any customer, subject and/or patient data, among others.

Some embodiments as described herein may be used in conjunction with and/or may benefit from information disclosed in pending patent application Ser. No. 12/434,244 filed May 1, 2009, entitled "Systems, Methods and Computer Program Products For Providing Compliant Messaging Services", the contents of which are incorporated by reference as if entirely set forth herein. Some embodiments described herein may be used in conjunction with and/or benefit from information disclosed in pending patent application Ser. No. 13/459,573 filed Apr. 30, 2012, entitled "Systems, Methods and Computer Program Products For Providing Compliant Delivery of Content, Applications and/or Solutions", the contents of which are incorporated by reference as if entirely set forth herein In some embodiments of the present invention, disease/condition specific mobile health solutions may be designed, built, delivered and maintained. Such solutions may provide dynamic support and management for a patient and be adaptive to support individual patient/consumer needs and/or preferences. Although some embodiments are directed to providing solutions to patients, some embodiments include solutions that are directed to using patient data to provide dynamic support and management for health care professionals, clients, payers and/or caregivers, among others. Although discussed herein in the context of healthcare such that target consumers may be patients, this disclosure is not so limited. For example, the methods, systems, operations and/or processes may be applied to other industries including agriculture, horticulture, animal management, industrial monitoring, executive and/or workforce performance management and/or monitoring, sporting and/or athletic performance management and/or monitoring, industrial processes, transportation, and/or network services, among others.

Embodiments disclosed herein may provide systems, methods and computer program products for providing personal care for a patient and/or user. For example, as described herein, patient treatment may be personalized by compliantly using personalized technology. In this manner, embodiments disclosed herein may dynamically launch mobile content, solutions and/or applications that are catered to user and/or patient specific needs, which may be identified in terms of individual and/or technological capabilities.

Reference is now made to FIG. 1, which is a block diagram illustrating operations for providing condition specific adaptive content according to some embodiments of the present invention. Operations include receiving condition specific information into a data repository (block 100). Some embodiments provide that the condition specific information includes health condition related data. For example, the condition specific information may include disease specific data. Sources for condition specific information may include one or more data repositories, services and/or publications regarding conditions and/or diseases, and disease findings.

Condition specific application requirements corresponding to the condition specific information may be defined (block 102). In some embodiments, the requirements may be defined, in part, via a mobile health request or identification provided by a health professional, such as a doctor, nurse, pharmacist, and/or therapist, among others. Defining such requirements may include selecting a disease and/or condition. As a disease and/or condition may include multiple different attributes, defining the requirements may include selecting one or more disease and/or condition attributes. Some embodiments provide that one or more functional components of the condition specific application may be selected based on which ones of the disease attributes are selected.

Once the functional components are selected and/or identified, the condition specific application may be built based on the requirements (block 104). The condition specific application may be built by defining function metadata corresponding to the one or more functional components of the condition specific application. Some embodiments provide that function elements may be defined based on the function metadata. Additionally, a function interface that corresponds to the functional components may be defined and/or generated.

The condition specific application may then be configured corresponding to one or more user-specific attributes (block 106). For example, user attributes may include communication related information and personal identification information. Examples of personal identification information may include names, gender, ethnicity, date of birth, place of birth, citizenship, subscriber identity module (SIM) card identifier, and/or residence information including street address, city, state and/or postal/zip code. Some embodiments of communication related information include a mobile terminal numerical or email address and/or phone number, the country or region (e.g., Canada, which has French and English languages) in which the mobile terminal is located and/or in which communication services originate, a language preference and/or media access control (MAC) addresses and/or ethernet hardware addresses (EHA) corresponding to wireless short range and/or NFC communications.

In some embodiments, configuring the condition specific application corresponding to user-specific attributes includes defining general rules and/or workflow corresponding to the condition specific application. Additionally, condition stages that are specific to the condition may be configured. In some embodiments, behavior stages of the user that correspond to condition stages may be mapped. Knowledgebase content may be mapped to the condition stages and/or the behavior stages.

In some embodiments, capabilities corresponding to the processing device, the user and/or a peripheral device may be assessed. The condition specific application may be packaged corresponding to the capabilities of the processing device, the user and/or the peripheral device.

Some embodiments provide that user information includes lists of installed and/or accessed applications and versions thereof. Additionally, user information may include identifiers corresponding to third party applications including, for example, Twitter, Skype, BlackBerry, and/or Facebook among others. User information may further include communication service terms including contract type (monthly, annual, prepaid, etc.), and a defined service area and/or areas identified based on signal strength and/or quality.

The condition specific application may be delivered to a processing device that is operable to execute the condition specific application (block 108). Additionally, the packaged condition specific application may be modified to include user specific data (block 110). For example, one or more components and/or operating modes of the condition specific application may be modified responsive to a change in the condition and/or user behavior.

The processing device may include a mobile and/or fixed terminal that includes and/or is communicatively coupled to at least one processor. Some embodiments provide that a mobile terminal may include a personal digital assistant (PDA), cell phone, pager and/or a machine that does not include a direct human communication interface in order to service a remote area and/or one in which a user may not have a persistent or reliable data connection, The mobile terminal may provide that mDNA data may be stored in a fixed memory location in the mobile terminal and/or may be stored in a removable media. Additionally, some embodiments provide that removable storage media may be used to transmit data to the mobile terminal using a physical delivery system.

Figure 2:
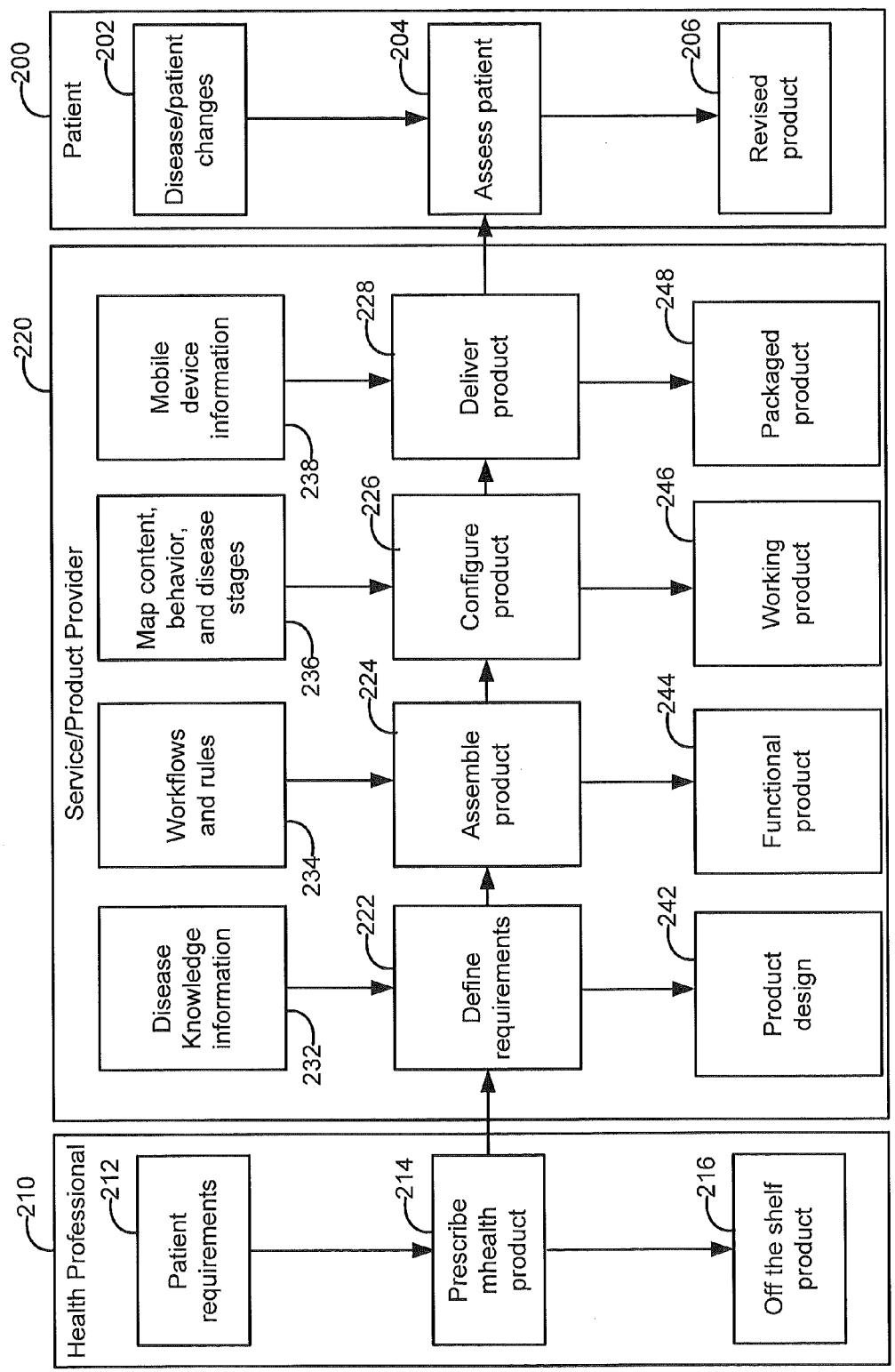
FIG. 2 is a block diagram that illustrates operations and workflow corresponding to systems and methods according to some embodiments of the present invention.

Reference is now made to FIG. 2, which is a block diagram that illustrates operations and workflow corresponding to systems and methods according to some embodiments of the present invention. Specifically, the diagram illustrates a high level view of systems, methods and computer programs for designing, building, delivering and maintaining a disease/condition mobile health solution that provides dynamic support and management specific to disease/condition. As illustrated, the development, provision and support of mobile health solutions may be divided into processes and their respective inputs and outputs, including possible roles of a health professional 210, a service/product provider 220 and a patient 200.

The health professional 210 may determine patient requirements 212 and prescribe a mobile health solution, also referred to as an mHealth product 214. In the event that an mHealth product has previously been developed to address the patient requirements identified by the health professional, then an off the shelf product may be provided 216. In the event that no off the shelf product is capable of meeting the patient requirements, then a service/product provider 220 may define the requirements for a disease or condition specific mHealth solution using disease knowledge information 232 and the patient requirements 212 identified by the health professional 210. An initial product design may be determined 242.

Once the requirements are defined the mHealth product may be assembled 224 using workflows and rules 234 corresponding to the product design, the disease or condition, and/or predefined processes. As a result of assembly, a functional product of the mHealth solution is ready to be configured 226 using mapped behavior and disease stages 236 to produce a working product 246.

Using mobile device information 238, the product is delivered 228 as a packaged product 248. Once delivered and/or implemented, the patient 200 is assessed 204 including determining disease and/or patient changes 202. In some embodiments, the product may be revised 206 responsive to the assessment 204.

Figure 3:
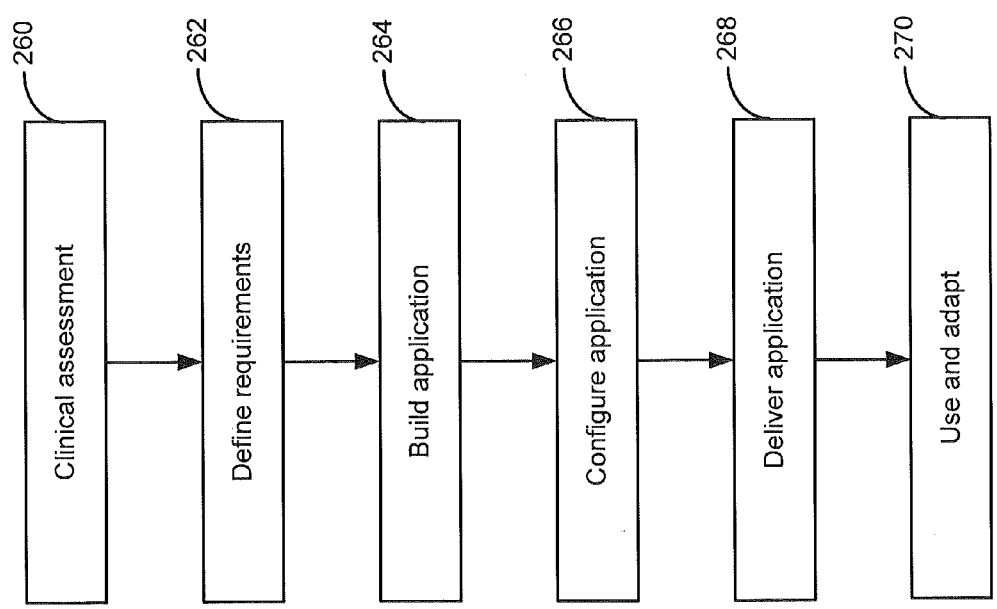
FIG. 3 is a flow diagram illustrating an overview of stages for providing an adaptive mHealth solution according to some embodiments of the present invention.

Embodiments as disclosed herein may support a whole life cycle of a mobile health solution from identifying the specifics of a disease or condition to building, configuring and verifying a mHealth solution, and then delivering and adaptively changing the solution when in use by a patient. For example, brief reference is made to FIG. 3, which is a flow diagram illustrating an overview of stages for providing an adaptive mHealth solution according to some embodiments of the present invention. The first stage includes clinical assessment (block 260). For patients enrolled onto a solution through a physician or clinical assessment, the health professionals may be integrated into the process, allowing the ability to specify, review and prescribe solutions.

This methodology allows for physicians and healthcare professionals to be involved in a mobile health solution's life cycle according to some embodiments herein. For example, a request or prescription for a mobile health solution can start with a physician looking to prescribe a solution on its own or in support of a patient's medication and/or treatment regimen. Requirements identified by a physician can therefore feed directly into the next 'Define' stage and then review the solution coming out of the 'Configure' stage. Any refinement coming out of the review can be cycled back through the system and/or approved for delivery to the patient.

Once the solution is in use by the patient, a physician or healthcare professional could continue to view patient or product progress and be directly involved in any remote solution adaptations. In some embodiments, solutions can maintain a full audit trail, providing a level of clinical validation to patient use and outcomes.

The next stage is the define requirements stage (block 262). In summary, solutions may be designed by matching industry classified conditions and published findings, with functional solutions that may be mapped from a disease knowledge base, which may include an internal and/or external data repository. In some embodiments, a solution design may start in this stage and may be defined with the support of two or more key data sources. For example, a first may be an internal 'disease findings' data repository maintained through a content syndication engine that extracts publications information on disease/condition research findings. Some embodiments provide that the syndication engine could identify published studies on Acute Coronary Syndrome medication adherence, including numerical and textual information on the key issues and potential solutions and strategies to overcoming the problems.

The second data source may include an internal 'disease knowledge base', which may be a comprehensive repository that captures evidence data on disease/condition solutions. This data repository is used in sync with configurations, content (described in the following stages) and findings repositories to connect evidence to working solutions and real world data. This data repository may include (but not limited to) how well each solution configuration works, by disease and demographics. The disease/condition classifications may be built on relevant industry codification standards, such as ICD (International Classification of Diseases).

The process of building a disease/condition solution may begin with selection of a disease/condition, from which the system can provide a list of key areas (herein referred to as disease/condition attributes or attributes) that need to be considered. For example, selecting Acute Coronary Syndrome might include the following in the list of attributes:
1. The need to address general state of health
2. Dealing with misbeliefs
3. Moody and emotional feelings are common
4. Forgetfulness is a common reason for medication non adherence From here, different solutions can start to be visualized by selecting different combinations of attributes in a solutions designer, which may include and/or be included in a user interface, such as, for example, a graphical user interface (GUI), among others. Some embodiments provide that the solutions designer is an automated builder used to create a number of solution mock-ups that can be individually rated. For example, in the above mentioned Acute Coronary Syndrome list, one scenario might be that all four attributes are deemed important and are all selected, while another scenario might only select attributes 3 and 4 in the list. The solution designer may provide a limited amount of configuration and sample content so the solution can be better visualized. Some or substantially all of the sample content may be automatically generated.

The solutions designer may then match a list of functional components that can address each of the key attributes selected. These functional components may include an overview explanation of how each disease/condition attribute can be addressed through the corresponding functional component, which can then be configured accordingly. For example, attribute 4, forgetfulness, will correspond to the alert/reminder component within the platform's software component library.

This section may also link to evidenced information and examples from the disease knowledge base and disease findings repository, providing important information in considering the merits of different functional components and configurations. For example, in Acute Coronary Syndrome, evidence might suggest the importance of building lifestyle change elements into any adherence solution for any real improvement in patients being able to better manage their condition in the long term. At the end of this process a final solution design may be selected.

Meta data from the define requirements stage may be used in the build application stage (block 264). The build application stage may provide further development of the software components. For example, each function starts as an empty framework based on decisions made in the define stage with the ability to construct the main workings through parameterized/scripted selections and/or instructions. It is at this stage that the rudimentary workings of each component may be defined. For example, if a planning and tracking component has been selected and is intended for use in supporting an acute coronary syndrome patient plan to manage a healthy living program, the function will be set up for health activity goal setting and tracking.

Most components may be selected from a modular library and then built out by defining specific metadata and selecting from a pre-defined set of parameters. More advanced capabilities may also be built through a non-technical scripting language. Some embodiments provide that the enhancement to existing and new components can be separately programmed and added to the modular library.

Previously constructed components can be re used for a new solution. Fully or partly constructed components can then be refined within the build and configure stages to create a new solution. The disease knowledge base and configurations repository (described in the Configure stage) can be used to adopt proven and tested configurations. At the end of this process all of the main components may be defined and constructed, and then may be transferred to the configuration stage where the specific rules, workflow and content workings are added to turn the solution into a fully useable product.

In some embodiments, the platform's library will hold an extensive and maturing set of components, a number of which may form a staple part of most mobile health solutions. The following is an example of just a few components.

Care Plan.

A recurring requirement in healthcare management is the need for patients to have an individual care or health plan. This function may provide each patient their own individual plan which could include (but not be limited to) key clinical data that patients should be aware of and a list of any personal goals that show progress and achievement. Care plans can form an important role in a patient's healthcare management, and as such can be configured and used in different ways. The care plan may ultimately be where everything comes together for the patient, in that they can see everything of importance to them in a centralized presentation. The care plan may also act as an important interface between the physician and patient.

Goal Management.

Central to a patient managing their healthcare may be the need to set goals that might be related to medication adherence, activity, lifestyle changes, psycho social barriers and/or any other factor that contributes to helping them better manage and Potentially improve their condition. When configured, these functions can be set up in an engaging form, for example, bringing an element of gamification (i.e. using gaming techniques to encourage people to perform healthcare related activities) to their activity targets by making them part of an interesting campaign to walk the equivalent of a marathon in a specified time.

Device/Sensor Integration.

Also central to mobile healthcare solutions may be the ability to integrate with medical and healthcare devices and sensors where appropriate. Such devices can be integrated into solutions utilizing industry standards wherever possible.

Further components may include assessment, reminders, education and/or reward, among others. These components could be delivered in a number of forms utilizing rich media, device technology/peripherals and social media where appropriate.

In addition to components described herein, systems and methods may be integrated into PHR/EHR solutions like Healthvault, as well as providing one or more API's to allow integration into the systems/methods. In some embodiments, third party components and/or configurations can form part of an extended library as well as adding evidenced findings to the disease knowledge base.

Once the build stage is performed, the application may be configured (block 266). For example, all functions may then be configured by mapping in stages of disease, behavior and medication (amongst others), as well as content, to create a complete working solution, Configurations may be built based on previous findings to provide effective patient engagement. During the earlier define stage (block 262), the previously described solution designer can be used to add a basic level of configuration and some sample content to help visualize the workings of the solution. In the configure stage (block 266), the configuration details and content may be more comprehensive and the selection of specific configurations and content may be supported by evidenced data from the disease knowledge base and/or an internal data repository for configurations.

In some embodiments, a configuration repository may capture metadata for configurations used on existing disease/condition solutions. Further still, results of patients using these configurations (i.e. how well the configurations worked) may be stored in the disease knowledge base. The disease knowledge base therefore may help configure solutions for a better patient outcome. With growing patient usage and increasing solutions, the disease knowledge base may be continually refining patient solutions. Some embodiments provide that results of the refined patient solutions may be published.

The configuration process may begin with a rules and workflows refinement, ensuring that all components function correctly and combine to work effectively. In some embodiments, solutions may be configured dynamically. For example, the solution may adapt to disease, condition, medication, patient, and/or other progressions (herein referred to as disease stages), so that content and actions adapt to better support the patient through these changes. For example, if a patient's condition changes, the solution will adapt to provide updated and relevant content and actions. Each of the disease stages may be defined by key data points that indicate a change. The data points may be mapped to rules that effect content and action changes.

Additionally, behavioral modification stages can also be mapped in a similar way. In some embodiments, behavioral modification may refer to patient's behavioral changes between different stages. Such changes may include denial and not dealing with their condition, accepting their condition but not yet dealing with it well, starting to get on top of managing their condition, and/or pro-actively managing their condition, among others. Behavioral modification stages may also be defined by key data points that indicate a change. The data points and/or the changes thereof may be mapped to rules that effect content and action changes. Behavioral changes might adapt content and/or actions to provide the right motivation and support offering the right level of behavioral re-enforcement.

To complete the configuration, a final pass is carried out that maps content into the solution. In some embodiments, content may include all the instructional and educational information. The content may be structured in a modular form so that it can be combined and consumed in multiple forms, for example, tip of the day, coping strategies, reminders, looking up advice, education and so on. The content may be mapped to the different components as well as disease and behavioral stages. Further, content can also be categorized and delivered by patient demographic, allowing for areas like language and reading age. Educational content can be adapted to individual patient's learning style. Content which is proprietary can be set up within the internal content repository for use in specified solutions and for specified time periods, as set out in the content's licensed terms of use.

Once the application is configured, it may be delivered (block 268). Some embodiments provide that patient device capabilities/user requirements may be assessed and an appropriately configured solution is uploaded. For example, systems and methods disclosed in above referenced pending patent application Ser. No. 13/459,573 filed Apr. 30, 2012, entitled "Systems, Methods and Computer Program Products For Providing Compliant Delivery of Content, Applications and/or Solutions" ("the mDNA system") may be used in the delivery of the application. For example, the mDNA system may be used to identify a patient's device, user and peripheral chromosomes, from which the most suitable solution configuration can be uploaded.

Any solution may be device agnostic and can be configured for access through one or more devices, including (but not limited to) cellular phone, tablet PC and internet TV, as well as being accessible through a browser based patient portal. From the outset, reference to a mobile health solution has referred to not just cellular device based solutions, but to a solution that is made individually accessible for each patient through the most readily available mediums. For example, physicians and health care professionals may use the portal to assess and/or review patients/solutions. It is also possible to extend any solution to individual caregivers and caregiver networks, providing patients extended support. At this stage the patient can access a sophisticated solution that has been designed and built to support them in the most comprehensive way. The patient can however further refine and personalize the solution adapting how it is utilized. This might include configuring how they interact with the solution or how they prefer to consume content. They may also be able to prioritize the how the solution works, focusing on what is most important to them. Finally, the patient may have some level of 'look and feel' configuration, allowing them to maybe change wallpaper, font, etc. The level of personalization may be set up during the build and configure stages, but may be later modified as well.

Importantly, the building and configuration of a solution prior to being delivered to a patient, as well as the level of configuration a patient can carry out, all work within safe working boundaries for the patient. This may be achieved through a combination of pre-defined parameters and a rules engine that can dynamically monitor and respond to changes.

After the solution has been delivered, the use and adapt stage (block 270) may provide a dynamic approach to adjusting content and actions. For example, once in use, the patient can be dynamically monitored, adapting functions and content according to a patient's progression. Some embodiments provide that adaptive elements are mapped into the core solution, enabling actions and content to be locally adapted. However, the systems and methods herein may also carry out remote assessment and updates.

Patient engagement or solution effectiveness can be assessed and updated remotely. Any such assessments and updates may be carried out within the strict bounds of customer terms and patient consent. Such remote assessments may work off of a patient consented, anonymized data repository. This repository may collate anonymized patient data, monitored for specific trends, e.g. content used by patients with the most successful outcomes. Remote updates can then be uploaded to relevant patient devices.

Regional patient consent and data privacy parameters may be fully captured and strictly tracked to provide that data is only collected and utilized for consented uses and maintained accordingly. Individual patient data may be assessed and solutions updated strictly within these parameters. Where appropriate, the consent/data privacy process can also allow patients to waive rights to local data protection law.

In addition to the locally provided solutions, systems and methods herein may be integrated into the broader healthcare ecosystem, integrating physicians and healthcare professionals, as well as healthcare systems and data. In some embodiments, integration may utilize adopted industry standards, which might include (but not limited to) ICD codifications and EHR/PHR standards/platforms. As well as supporting the development of new mobile healthcare solutions, the systems and methods herein can also be used to prescribe existing mobile healthcare solutions.

Systems and methods disclosed herein may support a range of users, including (but not limited to) patients, caregivers, payers, physicians and healthcare professionals. Each type of user can access relevant functions and data through a secure and customizable portal (in addition to any device access).

Figure 4:
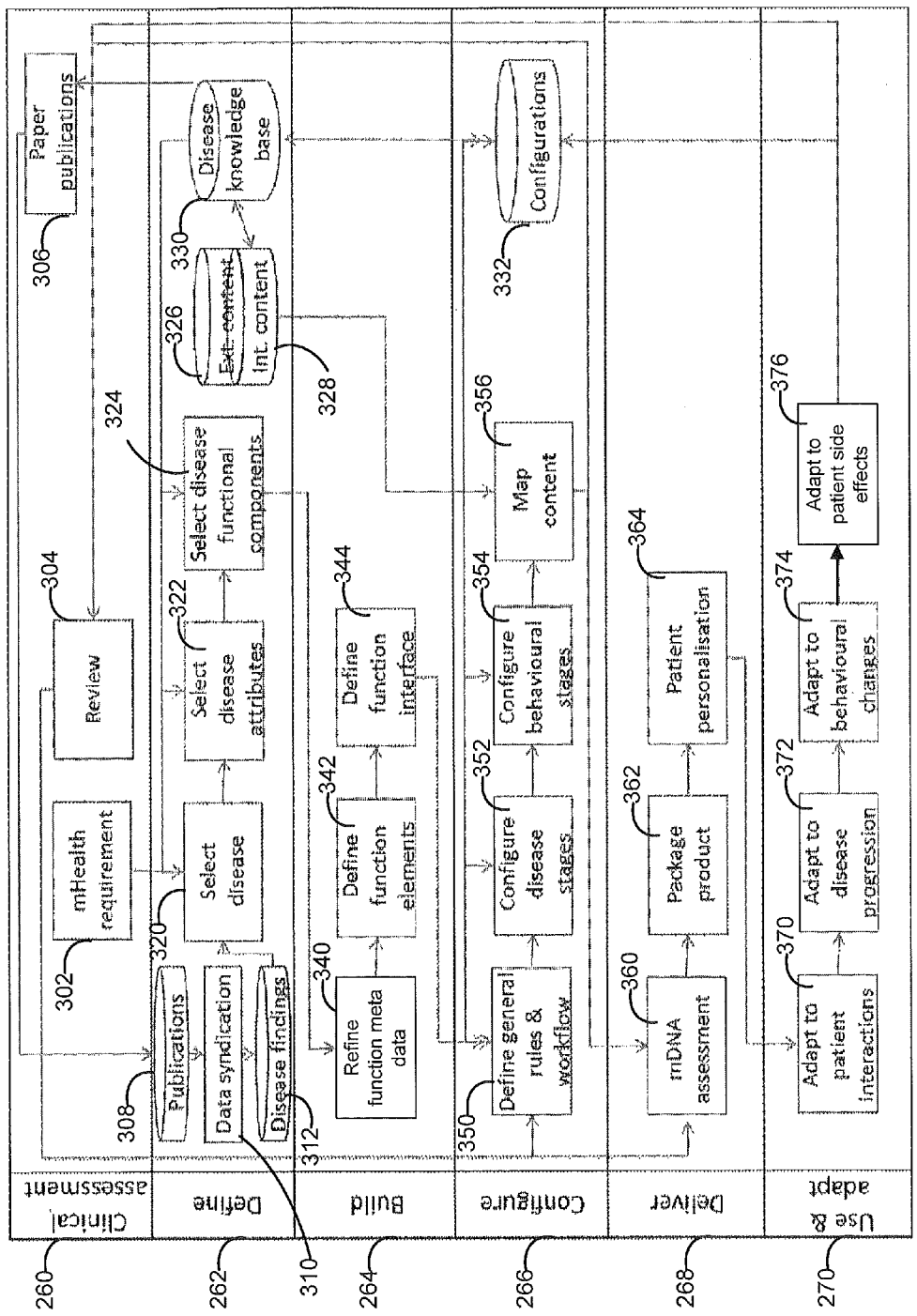
FIG. 4 is a flow diagram illustrating the stages described above regarding FIG. 3 including operations and flow therein according to some embodiments of the present invention.

Reference is now made to FIG. 4, which is a flow diagram illustrating the stages described above regarding FIG. 3 including operations and flow therein according to some embodiments of the present invention. The clinical assessment 260 may provide that an mHealth requirement is determined by a health professional 302. In the define stage 262, a disease may be selected 320 and information corresponding to disease findings 312 may be accessed and/or retrieved. The disease findings information 312 may be source from a data syndication 310, publications 308, including paper publications 306 and/or a disease knowledgebase 330 or other data repository. Once the disease is selected, disease attributes may be selected 322 and the disease specific functional components may be selected 324.

The build stage 264 may include defining the function metadata corresponding to the function components 340, the function elements 342 and the function interface(s) 344. In configuration 266, rules and workflow may be refined 350. The disease stages 352 and the behavioral stages 354 may be configured. Based on the configurations and internal and/or external disease specific content 326, 328, the content may be mapped. Additionally, the configurations may be stored 332.

In the delivery stage 268, the mDNA assessment 360 can be used to determine details regarding delivery of the solution. Based on the mDNA assessment, the product is packaged 362 and may be personalized for the patient 364. Once in use 270, the solution may adapt to patient interactions 370, disease progressions 372, behavioral changes 374 and/or patient side effects 376. Such changes may be reviewed 304 and the findings included in the disease knowledgebase 330.

Being an integrated part of a healthcare ecosystem, the systems and methods herein may support new workflows. For example, a physician can prescribe an existing mobile healthcare solution and then support a patient directly through the product. This may include reviewing a patient's progress through the physician portal, and then uploading changes to a patient's mobile device. Further still, care plans can form an integral part of any workflow, with care plans updated by a physician or healthcare professional after a patient review.

Figure 5:
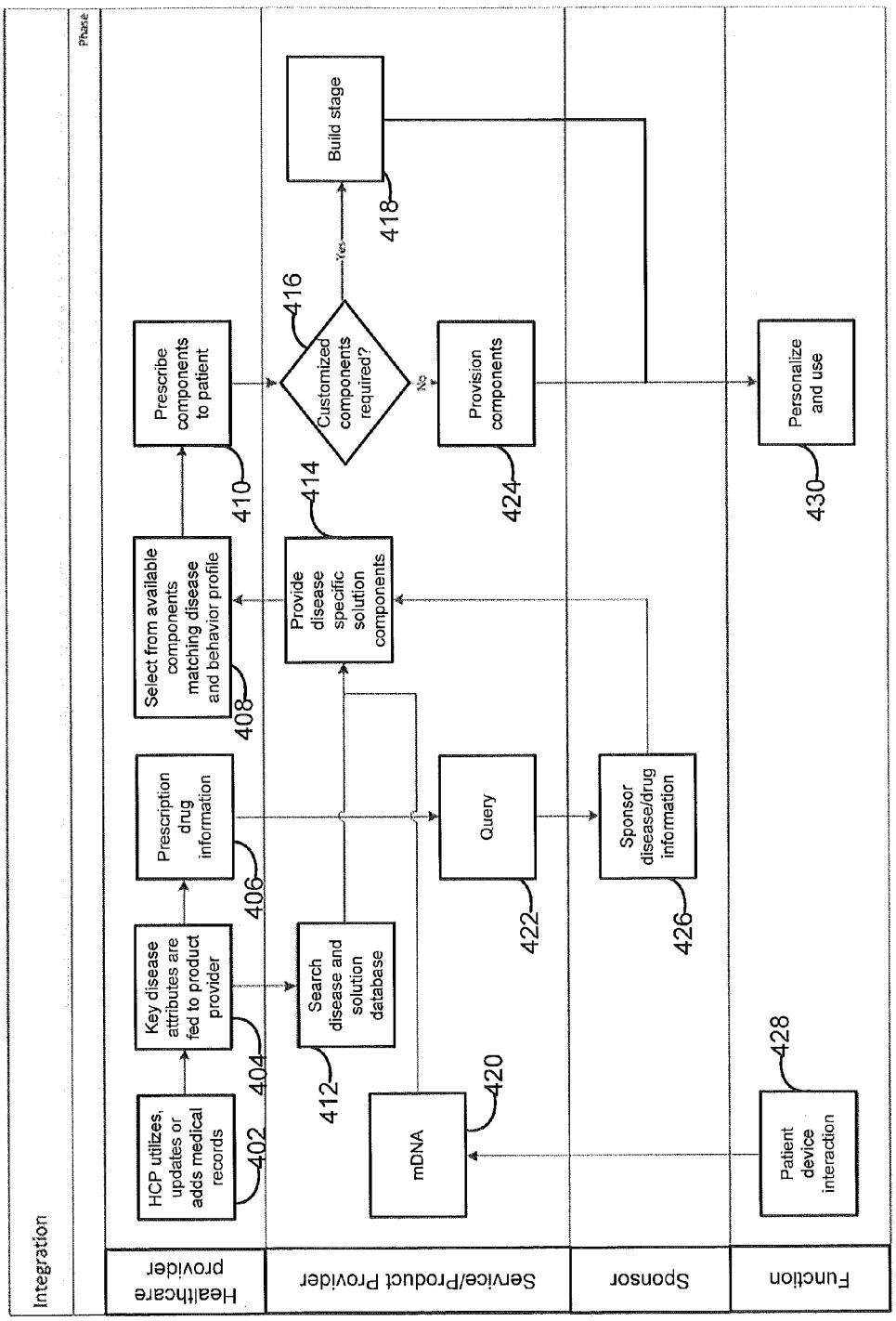
FIG. 5 is a block diagram illustrating operations and workflows corresponding to systems and methods as disclosed herein integrated within a healthcare ecosystem in accordance with some embodiments of the present invention.

An example integration across healthcare provider, solution provider and sponsor is shown in FIG. 5, which is a block diagram illustrating operations and workflows corresponding to systems and methods as disclosed herein integrated within a healthcare ecosystem in accordance with some embodiments of the present invention. This shows how a physician might also take into account prescribed drug needs, ensuring that a mobile health solution utilizes the right functions and configures them appropriately for patient use. Components may then either be built or selected from a library if already available.

Referring to FIG. 5, a healthcare provider may utilize, update and/or add a medical record to a data repository 402. Key disease attributes may be provided to a service and/or product provider 404. A disease and solution database that is provided, serviced and/or maintained by a service/product provider is searched 412. Additionally, based on the key disease attributes, prescription drug information is analyzed and/or determined 406.

Responsive to one or more patient device interactions 428, mDNA provides delivery specific information 420. The service/product provider may also query a sponsor 422 to determine sponsor provided disease/drug information 426. The service/product provider may provide disease specific solution components 414 responsive to the disease/drug information 426, the mDNA delivery specific information 420 and/or the search results from the disease and solution database 412.

The healthcare provider may select from available ones of the components matching the disease and/or behavioral profile 408 and prescribe components to the patient 410. A determination as to whether customized components are required is made 416. If customized components are required, then the build stage is employed to generate the customized components. Otherwise, previously generated components are provisioned 424 and then personalized and used 430.

By way of example, patient A is a fourteen year old boy with Cystic Fibrosis (CF), which is a life-threatening inherited disease. It is caused by a faulty gene that controls the movement of salt and water in and out of the cells within the body. CF affects the internal organs, especially the lungs and digestive system, by clogging them with thick sticky mucus. This may cause breathing and digestion difficulties. Previously about fifty percent of CF patients lived beyond 41 years of age, but with the support of healthcare solutions today, patient A may expect to live longer.

For example, when participating in a CF mHealth program, patient A and his parents may receive a comprehensive range of support mechanisms delivered directly to them. The requirement was initially identified by the family physician, when patient A was starting to rebel against the need for daily treatments. The requirement for a treatment, lifestyle and condition management solution identified an mHealth product that may provide the following disease specific support in the following manner.

First an mHealth product may include prescription and treatment management. In this manner, patient A may better manage both medications and treatments. He can set it up to remind him in the most appropriate way and time that his medications are due as well as monitor and manage prescription refills. Since daily physiotherapy treatments for patient A may be demanding, the mHealth product may assist the family in organizing and planning treatments in the most effective way.

Additionally, an mHealth product may provide nutrition and activity management. Good nutrition and an active lifestyle may be important factors in contributing to CF patients quality of life and longevity. As such, the nutrition management function may help patient A (and his parents) ensure appropriate nutrition. Additionally, the mHealth product may allows patient A to manage his caloric intake and ensure the right level of fat intake for his medication. The activity function may make exercise more engaging for patient A, for example, by allowing him to carry out activity events of interest within online social groups.

The mHealth product may include assessment functionality. For example, it may be important that CF patients monitor for any early indications of chest infection. The mHealth solution can help monitor both directly by looking for any signs of patient change and indirectly by carrying out short, regular assessments. Early identification of and early treatment of infections with antibiotics may prevent bacterial infections from establishing themselves and causing potentially irreversible damage.

Informational support and education may help patient A and his parents stay on top of his condition by providing them with the right information and education all the way through his life. This may be delivered in a variety of forms to ensure they get the right information in the right way at the right time, which might include tips of the day, coping strategies, education in new techniques and so on.

Additionally, a care/health plan can provide an easily accessible view of the information, goals, progress and achievements in an individual care plan. This information can be shared with health care professionals through an online personal health record (PHR) and/or a clinical electronic health record (EHR) as patient reporting information.

Further, caregiver support functions may allow caregivers to monitor patient A as well as being able to manage their own care activities and receiving caregiver specific information and support. The mHealth product may also adapt to changes. These might include patient A's own development into an adult, in which he legally takes responsibility for managing himself, as well as adapting to CF condition developments over time. It is also able to monitor for behavioral changes ensuring that both patient and caregivers are supported through difficult stages.

Figure 6:
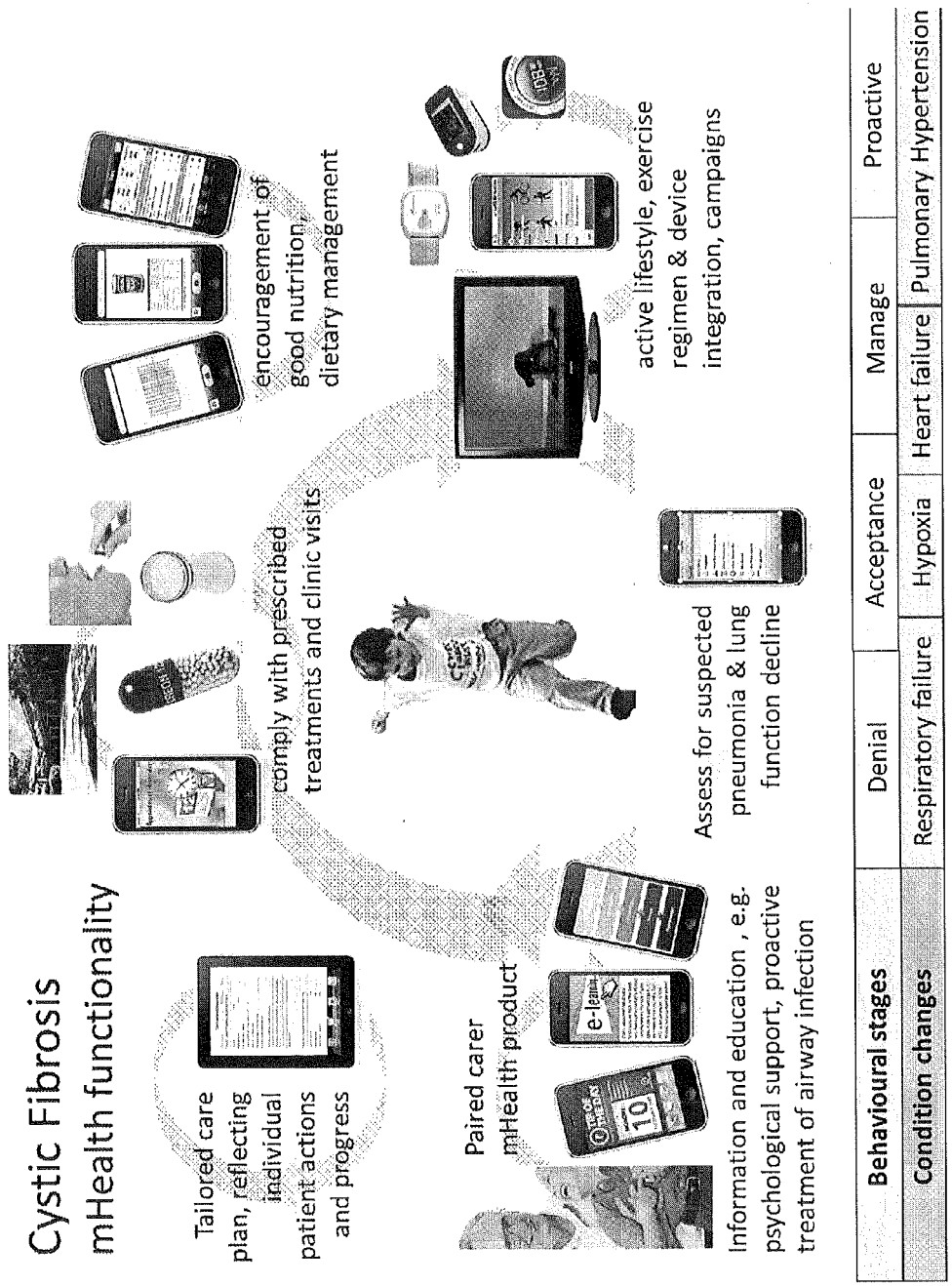
FIG. 6 is an illustration of the different functions and components in a CF specific mHealth product according to the example described above.

Patient A's family physician was able to identify a readily available CF mHealth solution. The physician is able to prescribe the solution directly through the mHealth platform and continue to monitor the patient's progress through the platform's physician portal. Brief reference is made to FIG. 6, which is an illustration of the different functions and components in a CF specific mHealth product according to the example described above.

Figure 7:
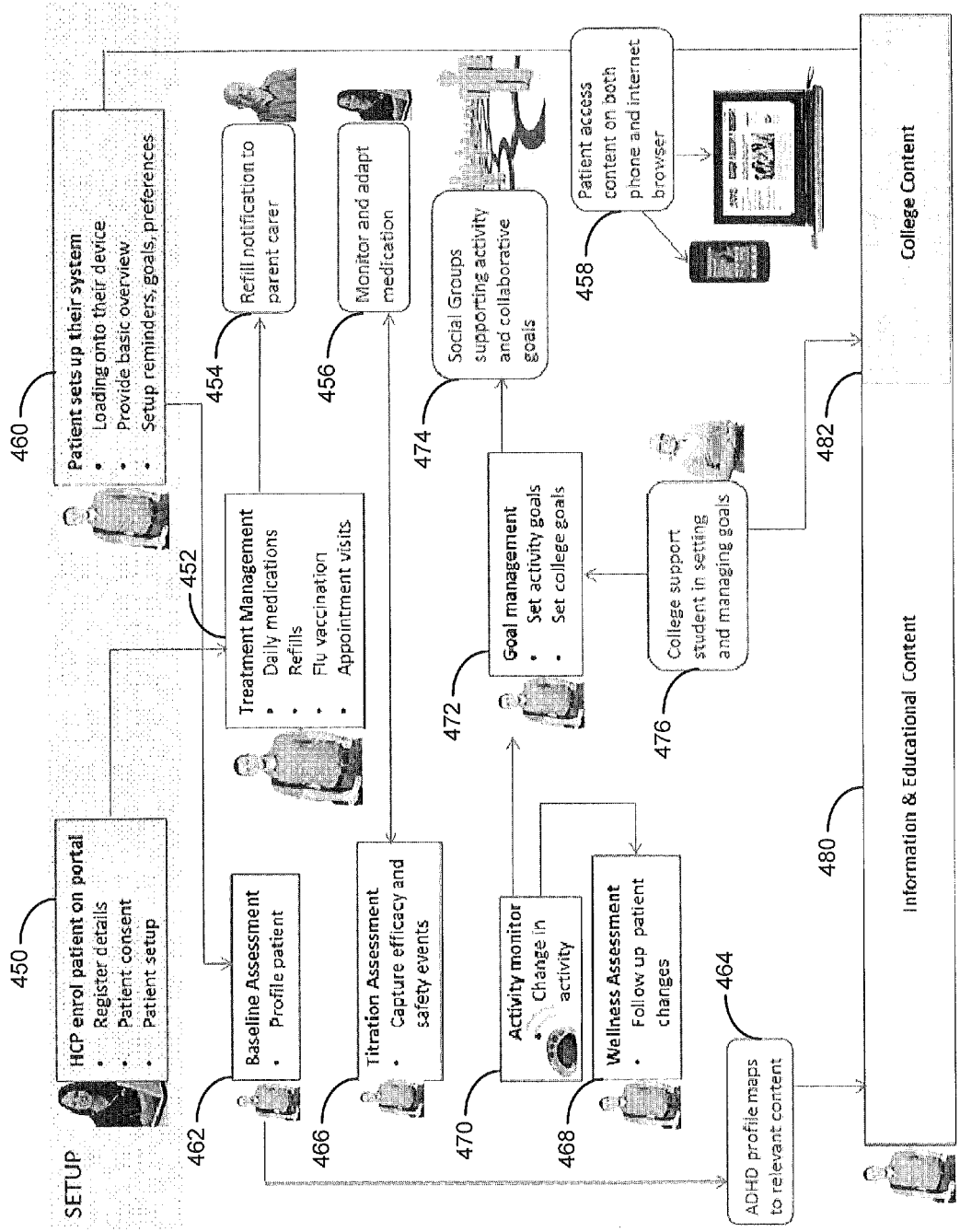
FIG. 7 is an illustration of different functions and components in an Attention Deficit-Hyperactivity Disorder (ADHD) specific product according to some embodiments of the present invention.

Reference is now made to FIG. 7, which is an illustration of different functions and components in an Attention Deficit-Hyperactivity Disorder (ADHD) specific product according to some embodiments of the present invention. By way of example, Patient B may be a seventeen-year-old male who has been diagnosed with ADHD and may be facing new challenges in self-management once not under the direct supervision of a parent or other caregiver. This example is presented as a product outline describing the range of functions that may be identified in effectively supporting ADHD patients. Some embodiments provide that patients would utilize their own mobile devices and existing network connections to access the systems and products disclosed herein. Additionally, systems methods and computer program products herein may further incorporate programs that rely on the support of third parties, including for example, parents, relatives, caregivers, teachers and/or healthcare professionals, among others.

Patients may enroll in the program via multiple different entrance points. Such entrance points may include direct registration by the patient, registration through a primary caregiver and/or registration through another institution, such as for example, a college or other educational institution. Some embodiments provide that functionality is designed to work around the patient, supporting them in achieving a greater degree of self-management and may be presented as a lifestyle tool that incorporates patient anonymity. For example, product functionality may be delivered in a manner that preserves the patient's self-esteem, while offering the patient an opportunity to more collaboratively engage others.

Some embodiments provide that a healthcare provider may enroll the patient via a portal corresponding to the systems and methods described herein (block 450). Enrolling the patient may include registering details corresponding to the patient and/or the patient health condition, evidence of and/or information corresponding to patient consent, and/or one or more different patient setup criteria.

A patient may set up their system and/or a profile corresponding to their system by loading one or more corresponding software modules onto a personal device (block 460). Some embodiments may include providing a basic overview of the system and receiving reminder data, goal data and/or preference data that may be used to configure the system. Once the system is set up, a baseline assessment may be established and may include a profile of the patient (block 462). The assessment function can cover a number of patient information capture and/or assessment operations. In some embodiments, a baseline assessment may be used to segment patients when first enrolling, allowing the system to then respond to different profile needs. For example such an assessment may be used to determine the patient's self-management readiness. In the setup stage, the patient may define personal preferences to further personalize their interaction.

Results of the assessment function may be used in combination with ADHD profile maps to determine relevant content (block 464). Content may include information and education content that may be mapped to the functions within the systems disclosed herein to deliver individual patients information that is relevant to their condition, that is presented in a meaningful way, and that is delivered in an order and at a time that may correspond to the relevant condition. In some embodiments content may include content from a pharmaceutical company that may be utilized in addition to additional externally provided material. In some embodiments, the content may include generic self-management material in addition to relevant ADHD condition specific information. For example, providing patients with an awareness regarding social skills may be delivered in the form of coaching.

Additionally, specific assessments may also be set up to run periodically and/or triggered by an event. For example, Patient B may have a pedometer that indicates that activity levels have reduced. This indication may trigger a simple assessment to determine how Patient B is managing. Other assessments may be set up corresponding to one or more specific purposes, for example, dose titration, which may be assessed to capture efficacy and/or safety events, among others (block 466). Depending on results from specific assessments, medication regimens may be monitored and adapted (block 456). In some embodiments, the specific assessments may be used in combination with a healthcare provider who may view efficacy and/or side effects via portal access, and adjust medication accordingly.

Treatment management data may be received, for example, via reminder data and content provided based on dynamic rules (block 452). In some embodiments, patient data may be used to set up medicine management protocols including medicine identifications, dosages, refill data, reminders, and/or cautions or warnings. Treatment management data may include an identification of medications, refill information, scheduled and/or proposed appointment visits, and/or medical record information such as vaccination records, among others. In some embodiments, refill notifications may also be sent to one or more other concerned parties, such as a parent or guardian of Patient B (block 454). Some embodiments provide that a treatment management function may include more than just traditional medication reminders. For example, patient non-adherence may often occur at the end of the series of issues that have cumulatively resulted in the patient deciding not to proceed further with medication. Such issues may include titration difficulties, concern over side effects, forgetfulness, misinformation and/or a lack of understanding. In this regard, a treatment management function may combine tools information and healthcare provider engagement to assist Patient B in managing their medication.

In some embodiments, one or more sensors and/or devices may be integrated into systems and/or methods disclosed herein. For example, in the context of Patient B having ADHD, an activity monitor such as a Bluetooth pedometer may be used to monitor a change in activity (block 470). Some embodiments provide that the activity may also be monitored using one or more accelerometers devices that may be included in a smartphone. The activity measure may be used as a monitor of the patient's state and may provide activity data for profiling the patient's movement profile from which the patient's different states may be mapped. For example, a wellness assessment may be performed based on the activity measure (block 468). In this manner, the patient's change in state may be detected in the systems and/or methods disclosed herein may provide a proactive response corresponding to changing needs.

The measure of activity may be used as a part of a patient's activity goals. For example a goal management function may allow patients to set and work towards personal goals (block 472). The build may be unique and may be provided by the patient and/or may be selected from predefined goals corresponding to, for example, ADHD. In some embodiments the goals may include goal programs for example dietary programs that contain meal information to help the patient work towards a better balanced diet. Additionally, goal programs may be linked to collaborative activities such as engaging patient and support networks (block 474). Additionally, systems, methods and computer program products herein may incorporate goal management tools that rely on support from external organizations and/or institutions, such as for example, a college or other educational institution (block 476).

Informational and educational content 480 may be combined with college content 482 and access by the patient using multiple different devices including smart phones, tablets, laptops, desktops, and/or other network and/or Internet capable devices (block 458).

Some embodiments provide that systems, methods and computer program products disclosed herein may incorporate and/or be supported by multiple different social media tools that may engage patients in collaborative groups. For example a simple support our mentorship level may connect the patient with a parent and/or teacher that may offer mechanisms for collaborative exchanges, monitor achievement, etc. These tools may be managed through one or more controlled social interaction products and/or may utilize more open social media products. In this manner, an ADHD patient may be provided with the ability to initiate participation in collaborative ventures, conversations and/or groups, among others.

In some embodiments, systems, methods and computer program products disclosed herein may be delivered in a manner that engages patients and may work towards applying a developing skill sets relevant to ADHD. For example, gaming techniques may be used to engage users and patients in achieving particular outcomes. In this manner, content may be delivered in a fun, relevant and engaging way.

By virtue of the systems, methods and computer program products disclosed herein, the patient who may otherwise be unwilling to have parents or relative caregivers directly monitoring and are supporting their self-management, may receive support from the parent or relative caregiver as collaborative support rather than parental monitoring. For example, the patient and parent may identify collaborative goals and activities to work on together. As part of this, the patient may then be willing to have a parent monitor drug adherence by providing a reminder and/or in support of aspects such as prescription refills. The parent or relative caregiver function may also be an effective support mechanism by providing help and strategies in supporting adult children.

Additionally, systems, methods and computer program products disclosed herein may extend to integrating and supporting educational institution programs. For example Internet portal access may allow schools and colleges to set up and incorporate their own ADHD programs, which might include a college's own support content, including, for example, effective strategies for the classroom, Some embodiments provide the teachers with an ability to work with ADHD students to agree and work toward specific goals using the systems and methods disclosed herein. Depending on the approach to implementation, schools and/or colleges may be directly involved in enrolling patients into the program, although teaching staff will have access to their students non-clinical patient information.

Additionally, systems, methods and computer program products disclosed herein may include a physician and/or other healthcare professional as an integral part of an ADHD solution. For example the physician or healthcare provider may enroll the patient into the program via a portal that includes patient consent, registration and set up within the system. In some embodiments, pharmaceutical companies may provide additional support in getting patients enrolled in such a program. An enrollment portal may provide a range of functions to help healthcare providers better support their patients. Such functions may include, for example, titration management, working with a patient self-management plan, and/or proactively monitoring patient progress, among others.

The data collected according to the systems, methods and computer program products described herein may provide significant real-time data resources that may be used by the system to profile individual and/or population level interactions, from which the system can adapt to provide more targeted and effective interventions. A body of anonymized population data may be gathered via the systems and methods herein and may provide additional significant insights regarding ADHD patient populations.

Figure 8:
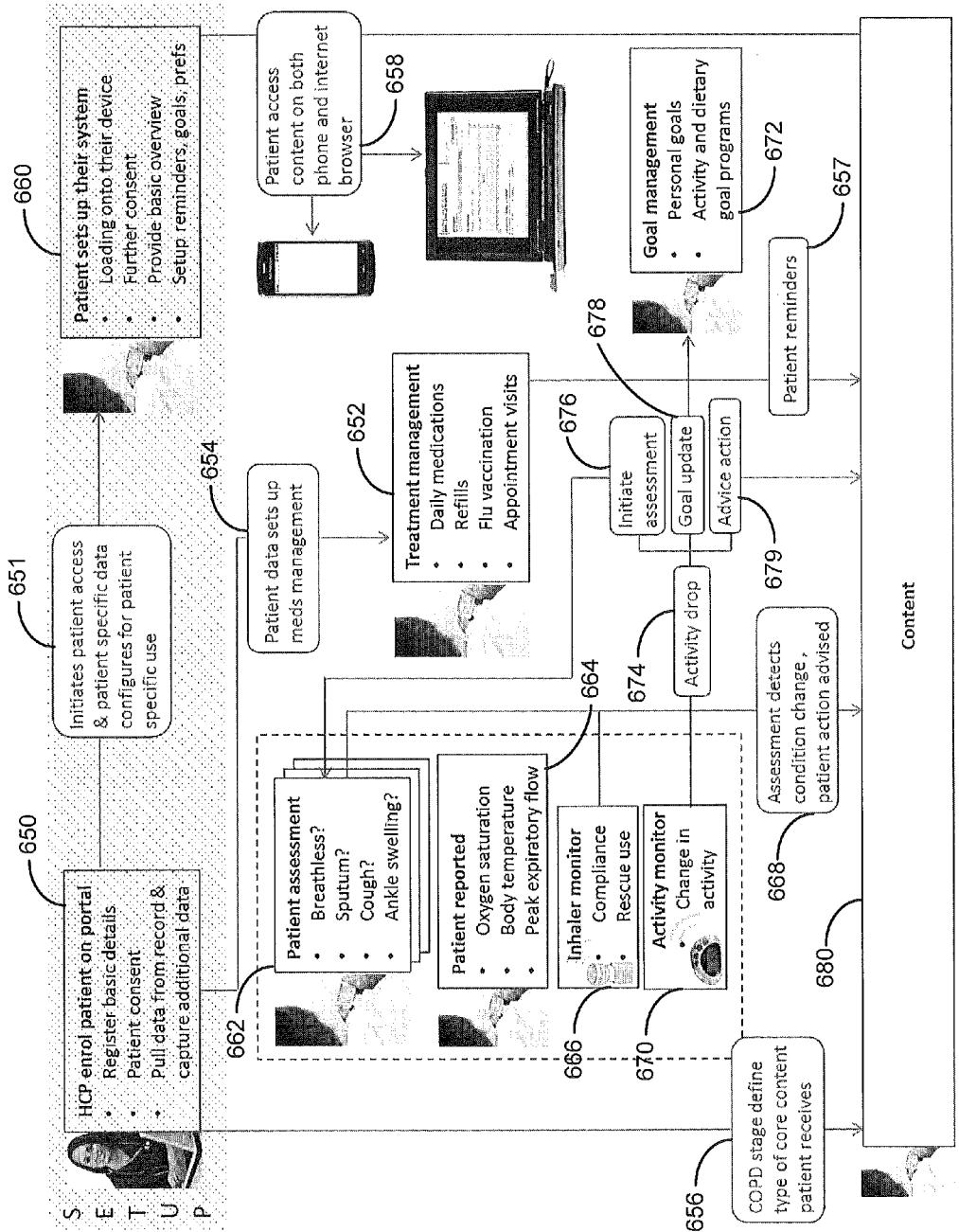
FIG. 8 is an illustration of different functions and components in a Chronic Obstructive Pulmonary Disease (COPD) specific product according to some embodiments of the present invention.

Reference is now made to FIG. 8, which is an illustration of different functions and components in a Chronic Obstructive Pulmonary Disease (COPD) specific product according to some embodiments of the present invention. By way of example, Patient C has been diagnosed with COPD. This example is presented as a product outline describing the range of functions that may be identified in effectively supporting COPD patients. Some embodiments provide that patients would utilize their own mobile devices and existing network connections to access the systems and products disclosed herein. Additionally, systems, methods and computer program products herein may further incorporate programs that rely on the support of third parties, including for example, parents, relatives, caregivers, teachers and/or healthcare professionals, among others.

Patients may enroll in the program via multiple different entrance points. Such entrance points may include direct registration by the patient, registration through a primary caregiver and/or registration through another institution. Some embodiments provide that a healthcare provider may enroll the patient via a portal corresponding to the systems, methods and computer program products described herein (block 650). Enrolling the patient may include registering details corresponding to the patient and/or the patient health condition, evidence of and/or information corresponding to patient consent, retrieving, receiving, capturing and/or entering medical and/or personal data. For example, data may be pulled from patient records and/or captured from other sources.

Patient access may be initiated and patient specific data may be configured and/or used to configure solutions as provided herein (block 651). A patient may set up their system and/or a profile corresponding to their system by loading one or more corresponding software modules onto a personal device (block 660). Some embodiments may include providing a basic overview of the system and receiving and/or providing reminder data, goal data and/or preference data that may be used to configure the system. In the setup stage, the patient may define personal preferences to further personalize their interaction. Additionally, further patient consent features may be incorporated.

In some embodiments, patient data may be used to set up medicine management protocols including medicine identifications, dosages, refill data, reminders, and/or cautions or warnings (block 654). Treatment management data may be received, for example, via reminder data and content provided based on dynamic rules (block 652). In some embodiments, patient data may be used to set up medicine management protocols including medicine identifications, dosages, refill data, reminders, and/or cautions or warnings. Treatment management data may include an identification of medications, refill information, scheduled and/or proposed appointment visits, and/or medical record information such as vaccination records, among others. Some embodiments provide that a treatment management function may include patient reminders (block 657).

A patient assessment may be established and may include clinical assessment (block 662). The assessment function corresponding to COPD may cover a number of patient information capture and/or assessment operations. In some embodiments, a patient assessment may assess different physiological functions and/or conditions such as a degree of breathlessness, the presence or characteristic of sputum, type and frequency of cough, and/or ankle swelling among others. Patient reported data may be received and may include oxygen saturation, body temperature and/or peak expiratory flow, among others (block 664). Additionally, an inhaler monitor may provide data corresponding to compliance and/or rescue use (block 666).

In some embodiments, one or more sensors and/or devices may be integrated into systems and/or methods disclosed herein. For example, in the context of Patient C having COPD, an activity monitor such as a Bluetooth pedometer may be used to monitor a change in activity (block 670). Some embodiments provide that the activity may also be monitored using one or more accelerometer devices that may be included in a smartphone. The activity measure may be used as a monitor of the patient's state and may provide activity data for profiling the patient's movement profile from which the patient's different states may be mapped. For example, in the case that Patient C experiences an activity drop (block 674), systems and methods herein provide that an assessment may be initiated (block 676), an activity goal may be updated (block 678), and/or an advice action may be generated (block 679), among others.

The assessment and/or data collected therefore may be used to detect a condition change and/or provide an advised action for the patient (block 668). In this manner, the patient's change in state may be detected in the systems and/or methods disclosed herein may provide a proactive response corresponding to changing needs.

Data corresponding to the enrollment operations may also be used to define the type of core content that a patient receives based on the stage of the patient's COPD (block 656). The defined content 680 may be accessed by the patient using multiple different devices including smart phones, tablets, laptops, desktops, and/or other network and/or Internet capable devices (block 658). The content 680 may include information and education content that may be mapped to the functions within the systems disclosed herein to deliver individual patients information that is relevant to their condition, that is presented in a meaningful way, and that is delivered in an order and at a time that may correspond to the relevant condition. In some embodiments, content may include content from a pharmaceutical company that may be utilized in addition to additional externally provided material. In some embodiments, the content may include generic self-management material in addition to relevant COPD condition specific information.

Additionally, systems and methods disclosed herein may include goal management functions that may allow patients to set and work towards personal goals (block 672). The goals may be unique and may be provided by the patient and/or may be selected from predefined goals corresponding to, for example, COPD. In some embodiments, the goals may include goal programs, such as, for example, activity and/or dietary programs that contain meal information to help the patient work towards a better balanced diet.

The data collected according to the systems and methods described herein may provide significant real-time data resources that may be used by the system to profile individual and/or population level interactions, from which the system can adapt to provide more targeted and effective interventions. A body of anonymized population data may be gathered via the systems and methods herein and may provide additional significant insights regarding COPD patient populations.

Some embodiments of the present invention provide that the patient portion of the system may focuses on supporting the patient to better self-manage their condition. In this regard, the system can be set up to monitor and support the patient with the aim of identifying early indications of exacerbation and preventing hospital or clinic visits.

Assessment and/or monitoring may be provided using methods and systems described herein. The level and type of patient direct assessment may be targeted at a maintainable level for the patient and may be designed to make information capture as easy as possible. Some embodiments provide that these direct assessments can be supported with background monitoring, in which key parameters are identified and monitored for change. In some embodiments, patients may be prompted at pre-defined intervals and/or based on patient outcomes, e.g., increased use of rescue treatment, reduced activity. A range of different assessments designed for pre-determined patient triggers and/or as periodic checks may be generated. As discussed above, information requested might include sputum rating, cough properties, ankle swelling, breathlessness, and/or a symptom score, among others.

Some assessments might capture medical device readings, which the patient may read from the device and capture manually, e.g. oxygen saturation, body temperature, lung function. Data may also be captured directly from wireless medical devices. As with general assessments, medical device readings may be prompted at pre-defined intervals and/or based on patient outcomes. Wireless devices might include inhalers or pedometers. The system may receive external environmental data on regional pollen count and air pollution to provide patients alerts and advice when levels are at a level that could impact the patient.

Some embodiments provide that patients can be assessed directly (explicit assessments) to identify any change in behavioral state and/or indirectly (background monitoring) based on pre-identified parameters. This data may be used to support patients and may include encouragement, promotional programs and reduced risk. Specific behavioral intervention models may be adopted, including, for example:

Health belief model, in which patients alter health related behavior according to perceived severity Relapse prevention model, which promotes prolonged healthy behavior by making distinctions between lapses and re-lapses I-Change model, built around awareness, motivation and action As part of background monitoring, the system may capture patient usability data, which can be used as key parameters in helping identify behavioral changes.

A treatment management function may support a patient in managing all aspects of their clinical treatment, including medication, vaccinations and clinic visits. A patient may have the ability to set preferences in how the system reminds them to take medications and confirm they have done so. Multiple different types of medication can be included, e.g. pills, inhaler medications, liquids, suspensions, epidermally applied medicines and/or oxygen therapy, among others. In some embodiments, the patient may receive informational and education support via the system to help understand important information related to their medication(s).

In some embodiments, systems and methods described herein may allow a patient to define the quantity of available pills and/or activations and countdown against usage, advising ahead of time when refills are due. Refills may then be confirmed and counters appropriately reset.

In some embodiments, systems and methods herein may prompt a seasonal flu vaccination reminder if appropriate. An individual patient's flu vaccination status may be maintained, which may be updated by the patient. Such functionality may further be supported by flu information, e.g. when advising to book a flu vaccination, the patient may be provided with information on why this appointment is so important to COPD patients.

Some embodiments provide that a clinic visit management feature may provide functionality through which a patient may set personal appointment reminders. These appointments may be identified by appointment type and may be supported by corresponding information related to the type of appointment. For a pulmonary rehabilitation appointment, in addition to reminders, the patient may receive supporting information relevant to their stage of the program, e.g. "well done Tom, you have nearly completed your PR program, your final visit is next Monday at 10 am."

Some embodiments provide a goal management function that provides patients the ability to set goals/objectives. As such, patients may be enabled to define their own personal goals, provide a predefined list of goals (e.g. dietary goals could include, 5 fruits and vegetables a day, sufficient daily fluids), and/or provide programs that support specific goals (e.g. a specific exercise program that a patient can follow, perhaps in support of their pulmonary rehabilitation). For example, a patient may set themselves the goal to increase their daily step count, which would be based on guidelines the patient is provided about activity. The patient may set themselves the target of walking to a specific destination daily, which may ensure they cover a minimum quantity of steps per day. If the patient carries a wireless pedometer, the pedometer may monitor the patient's activity and may provide encouragement and/or recognition of their achievements. Some embodiments provide that goal management may include common goals, like quitting smoking, but may refer the patient externally to supporting content or programs.

In some embodiments, content in the system may be provided by multiple different inputs including the data collected. Additionally, the system may provide multiple different outputs, which may be the information presented to and/or provided to the patient. The latter, which is referred to here as content, represents all the information and education content which a patient may receive and/or access according to systems and methods herein. Content to be used in the system may be sourced from a combination of sources. For example a systems mapping exercise may provide that available and required content would be mapped against profiles, rules and/or events to ensure that patients receive a combination of routine content and outcome based content.

Figure 9:
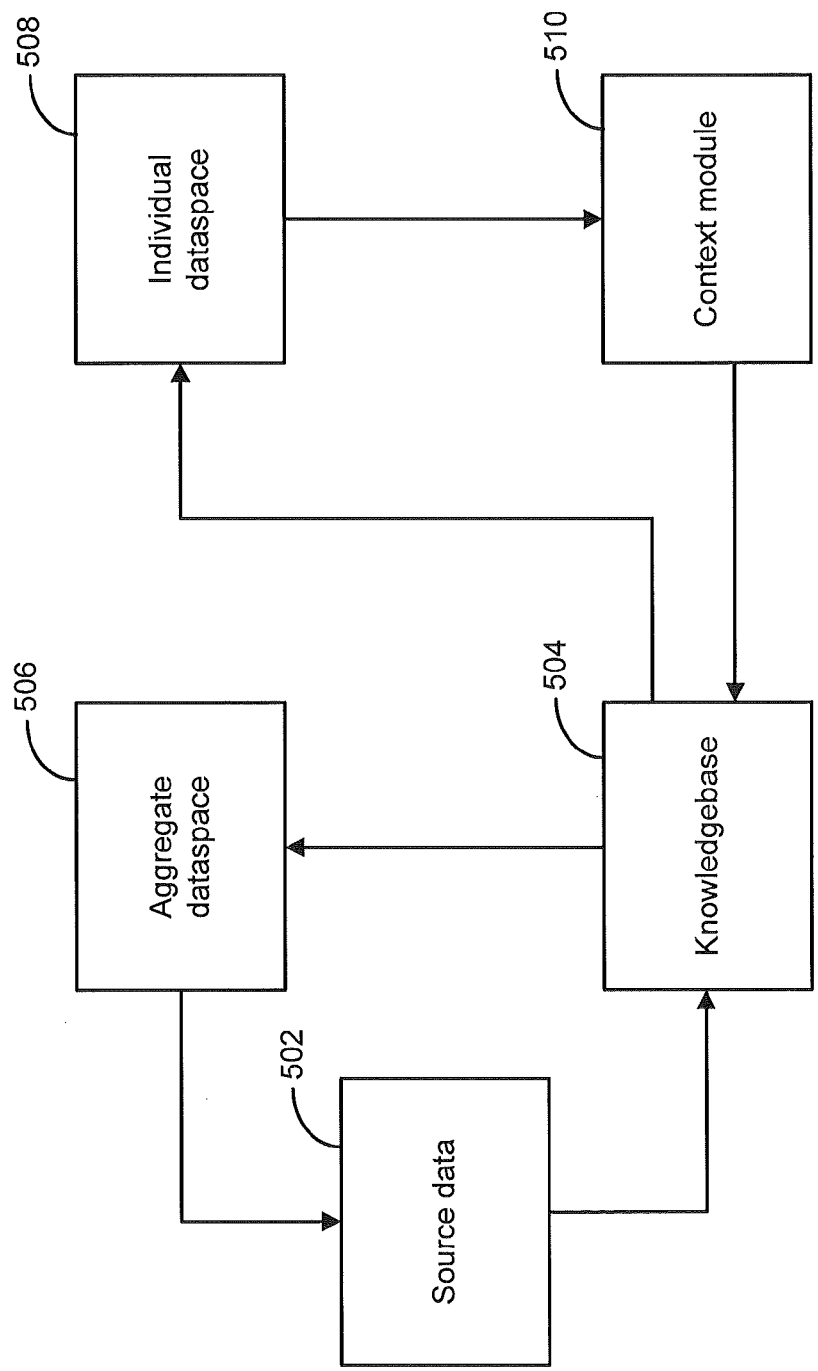
FIG. 9 is a block diagram illustrating systems/methods/operations for providing condition specific adaptive content according to some embodiments of the present invention.

Reference is now made to FIG. 9, which is a block diagram illustrating systems/methods/operations for providing condition specific adaptive content according to some embodiments of the present invention. A knowledgebase 504 may include one or more data repositories that includes content that is acquired, stored and/or maintained corresponding to one or more conditions. For example, in the healthcare context, the content may include a knowledgebase containing metadata corresponding to healthcare conditions including disease and/or condition information. The knowledgebase 504 may be configured to receive source data 502 from one or more external data sources 502 and/or types of data sources. An individual dataspace 508 may include data corresponding to an individual instance. For example, in the healthcare context, an individual data space 508 may correspond to a specific patient. In this regard, the individual dataspace 508 may also be viewed as a personalized dataspace. In some embodiments, data in the individual dataspace 508 may be encrypted before transmission, during transmission, upon receipt and/or before storage therein. Some embodiments provide that the individual dataspace 508 may receive data that has been de-identified from a corresponding individual prior to receipt and storage. In this regard, while the individual dataspace may be personalized regarding the data, such personalization may be stored without any identification of the corresponding person.

In some embodiments, data corresponding to the individual dataspace 508 may be used by a context module 510 to generate a context corresponding to the individual. The context may be used by the knowledgebase 504 to generate a solution, process and/or plan to be applied in the individual dataspace 508. Additionally, changes corresponding to the individual dataspace 508, such as metrics corresponding to the solution, process and/or plan may be provided to the context module 510 to identify any changes in the context, which may be reprocessed within the knowledgebase 504 to modify the solution, process and/or plan responsive thereto.

While the individual dataspace 508 may include data corresponding to an individual entity, an aggregate dataspace 506 may also receive content from the knowledgebase 504. In such cases, the content may be completely anonymized and delivered as aggregate data. In some embodiments, the aggregate data may be processed and/or analyzed in the aggregate dataspace 506 and results therefrom may be provided back to the knowledgebase 504 to enhance, supplement, replace and/or improve the data therein.

In some embodiments, an audit trail may be generated corresponding to the personal dataspace 508, the aggregate dataspace 506 and/or the source data 502. For example, an audit trail may be used to determine deletions, additions and/or modifications of data, including time and date information and identification of the responsible entity.

Some embodiments provide that the data content and/or the data format in the personal dataspace 508, the aggregate dataspace 506 and/or the source data 502 may be encrypted to guard against misuse of the data.

Figure 10:
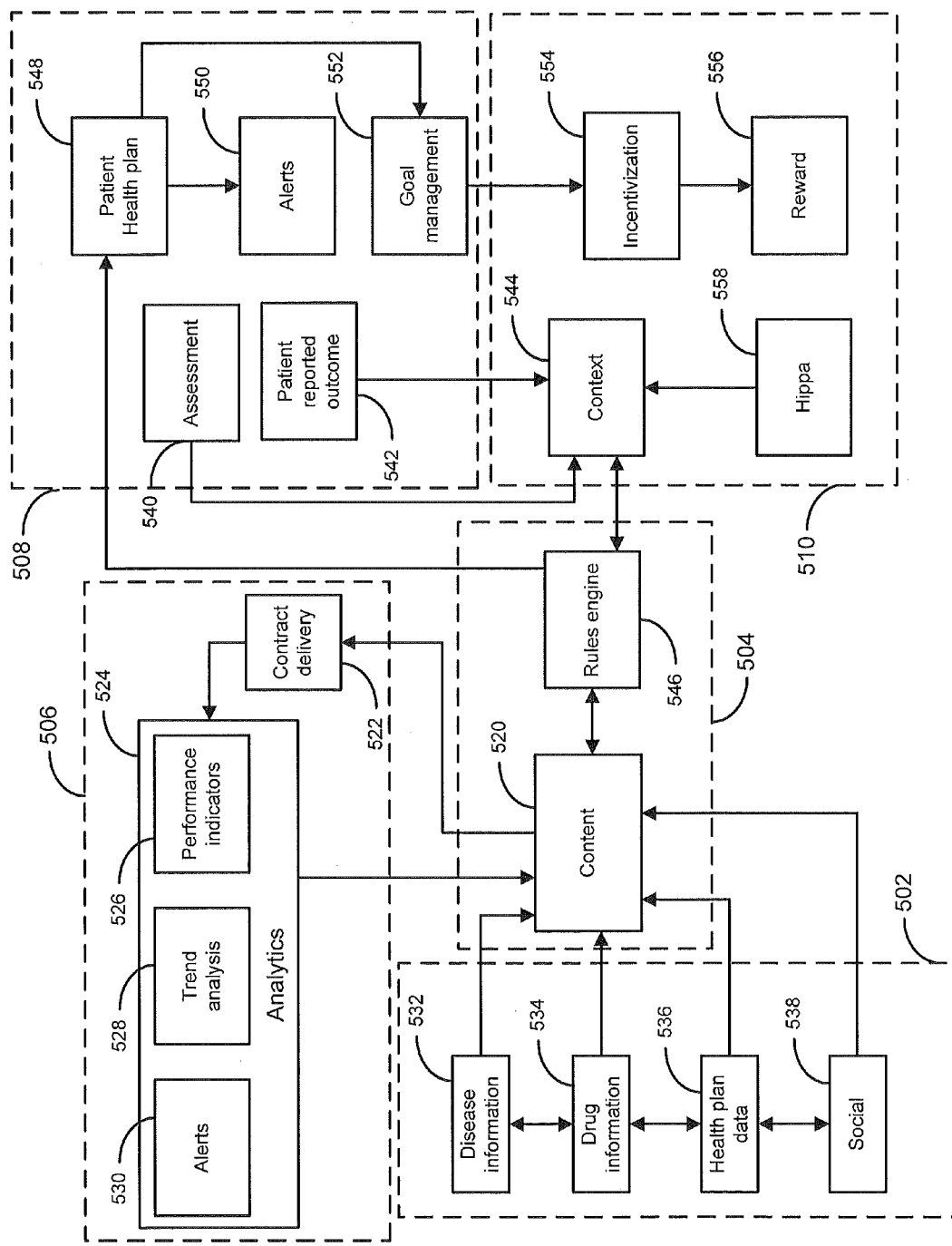
FIG. 10 is a block diagram illustrating systems/methods/operations for providing condition specific adaptive content according to some embodiments of the present invention.

Reference is now made to FIG. 10, which is a block diagram illustrating systems/methods/operations for providing condition specific adaptive content according to some embodiments of the present invention. Content 520 may be acquired, stored and/or maintained corresponding to one or more conditions. As used herein, content 520 may include text data such as articles, numerical and/or alphabetic data, graphical data including images and/or video content, and audio content that may be delivered and/or stored using any of a variety of formats and/or protocols. For example, in the healthcare context, the content 520 may include a knowledgebase containing metadata corresponding to healthcare conditions including disease information 532 and drug information 534. Disease information 532 may include multiple different parameters that further differentiate properties of the respective diseases and/or conditions. Drug information 534 may include information about specific drugs including their capabilities, usage in treatment of specific diseases and/or conditions, contra-indicators regarding diseases, conditions and/or treatments, and historical data including performance indicators, among others. The disease information 532 and/or the drug information 534 may be received from one or more external sources of data including, for example, electronic and paper publications, syndicated data sources and/or disease findings among others.

Some embodiments provide that health plan data 536 that corresponds to and/or is associated with one or more diseases and/or conditions and may be included in the content 520. For example, health plan data 536 may identify and/or define dietary plans and/or exercise regimens that correspond to one or more diseases and/or conditions. Additionally, social media information 538 regarding health plan, disease, drug and/or condition data that may also be included in the content 520. Social media information 538 may include a variety of social media types that include content specific pages, sites, blogs and/or online communities, among others. As illustrated, the disease information 532, drug information 534, health plan data 536 and/or social media information 538, may be collectively referred to as the source data 502, as discussed above regarding FIG. 9.

An individual assessment 540 may provide data and or information that is specific to the corresponding individual. In the context of healthcare, the individual dataspace 508 may include data generated in an assessment 540 of the patient to determine specific data corresponding to that patient. For example, identified diseases, conditions, and/or medical data may be determined in the assessment 540. In some embodiments, patient genomic information may be included in the assessment. In this regard, the content 520 may include pharmacogenomics data that may further personalize a patient health plan 548. In some embodiments, the genomic information may be used to identify and adapt a preventative solution corresponding to factors in the genomic information.

Another form of individual data may include patient reported outcomes 542, such as responses to treatments and/or changes in conditions and/or diseases, among others. Patient reported outcomes 542 may include responses to surveys and/or questionnaires that a patient may answer singularly and/or periodically over a period of time.

The information from the assessment 540 and the patient reported outcomes 542 may be used to form a context 544 of the individual. The context 544 may be generated in the context module 510 as discussed above regarding FIG. 9. The context 544 may be used in combination with the content 520 by a rules engine 546, which may deliver a patient health plan 548 that is specific to that patient with that disease and/or condition. The patient health plan 548, which may be in the individual dataspace 508, may help the patient manage their own health in a disease and/or condition specific manner. For example, exercise regimen, drug adherence information, drug reminders, alerts, diagnostic reminders, text messages, etc. For example, the patient health plan may be delivered to the patient and may include incoming and outgoing messages corresponding to and in addition to the other content 520.

Additionally, goal management 552 may include support for setting certain goals corresponding to the patient health plan 548. A patient may use the goal management 552 to track their individual performance against goals that correspond to the patient health plan 548. Goal management 552 may be used in conjunction with incentivization 554 to assist the patient in managing and reaching goals corresponding to the patient health plan 548. Incentivization 554 may include and/or be implemented with one or more reward plans and/or systems 556. Incentivization 554 and reward 556 may be included in the context module 510 and may optionally provide data to further refine the context 544.

Additionally, regulatory compliance requirements may vary among different individuals, based on conditions, data, and/or jurisdictions, among others. As such, the context 544 may also be determined using data corresponding to regulatory regimes, such as, for example, HIPPA 558.

The content 520 may also be provided via a contract delivery 522 module. In such cases, the content may be completely anonymized and delivered in an aggregate dataspace 506. In the aggregate dataspace 506, analytics 524 may be used to provide alerts 530, trend analysis 528 and/or to generate and/or monitor relative to one or more performance indicators 526. Further, some embodiments provide that results of the analytics 524 may be provided back to the content 520 to further enhance the data therein.

Figure 11:
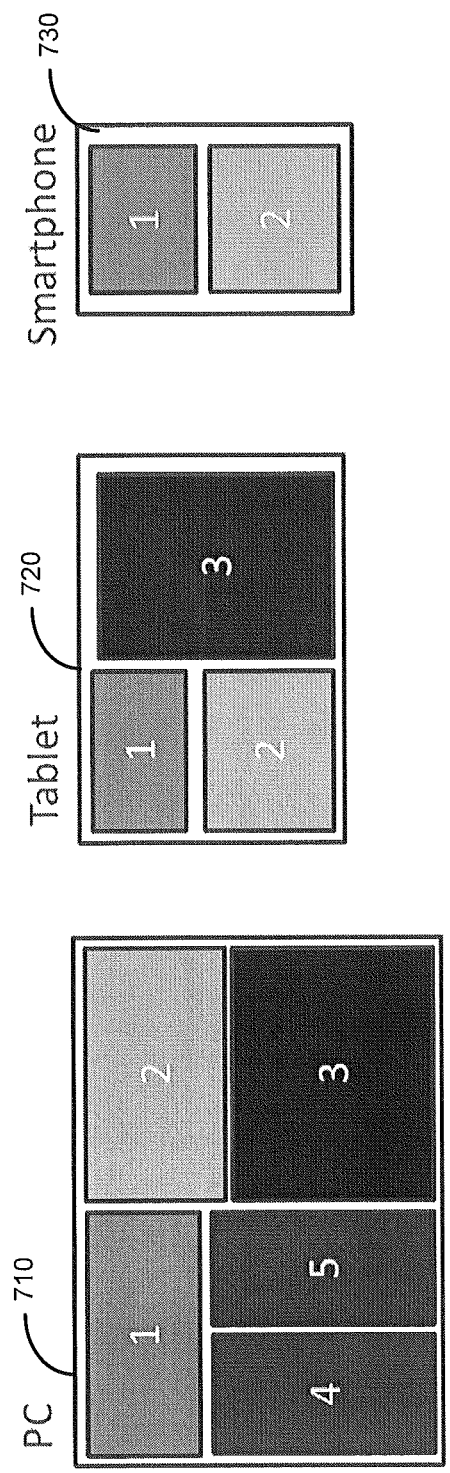
FIG. 11 is a block diagram illustrating different access portal layout screen configurations corresponding to different classes of electronic devices through which a patient may access systems provided according to some embodiments disclosed herein.

Brief reference is now made to FIG. 11, which is a block diagram illustrating different access portal layout screen configurations corresponding to different classes of electronic devices through which a patient may access systems provided according to some embodiments disclosed herein. Systems and methods herein, which may also be referred to as solutions, may provide different portals that correspond to the different conditions and/or diseases. For example, a COPD program online portal may be used to enroll a COPD patient by a health care professional or provider. Some embodiments provide that the health care professional may receive and provide any requisite consent operations before capturing initial patients detail and/or determining any baseline assessment. A system portal may provide a primary access point for a number of different users and/or types of users. Some embodiments provide that users may access the portal through a standard internet web browser, however this is by way of non-limiting example. Patients can access much of the functionality and content on mobile devices through the portal. The system may utilize available screen size as effectively and appropriately as possible. For example, as illustrated, a PC display 710 may provide significant amounts, types and granularity of information and/or access via different user interface regions 1-5 that may be usefully displayed thereon. A tablet display 720 may provide less available screen area and thus the portal may adjust the interface to display only interface regions 1-3. Similarly, a smartphone display 730 may be significantly more limited in available screen area and thus the portal may only display interface regions 1 and 2.

In this manner, although a patient would benefit from using much of the key functionality through their mobile device, they are able to both capture and consume information through logging into a system portal. In the same way that key day to day patient interactions (interface regions 1 and 2) are designed for optimal use through their mobile device, patients might prefer to consume some of the richer media content (interface regions 3-5) through the larger browser based portal.

Some embodiments provide that a complete set of anonymized population data may be available to provide a detailed view of patient parameters, activity, interaction and/or outcomes. Essentially, all de-identifiable population data may be available to analyze. This anonymized data may be located and/or stored separately and transactionally updated.

Figure 12:
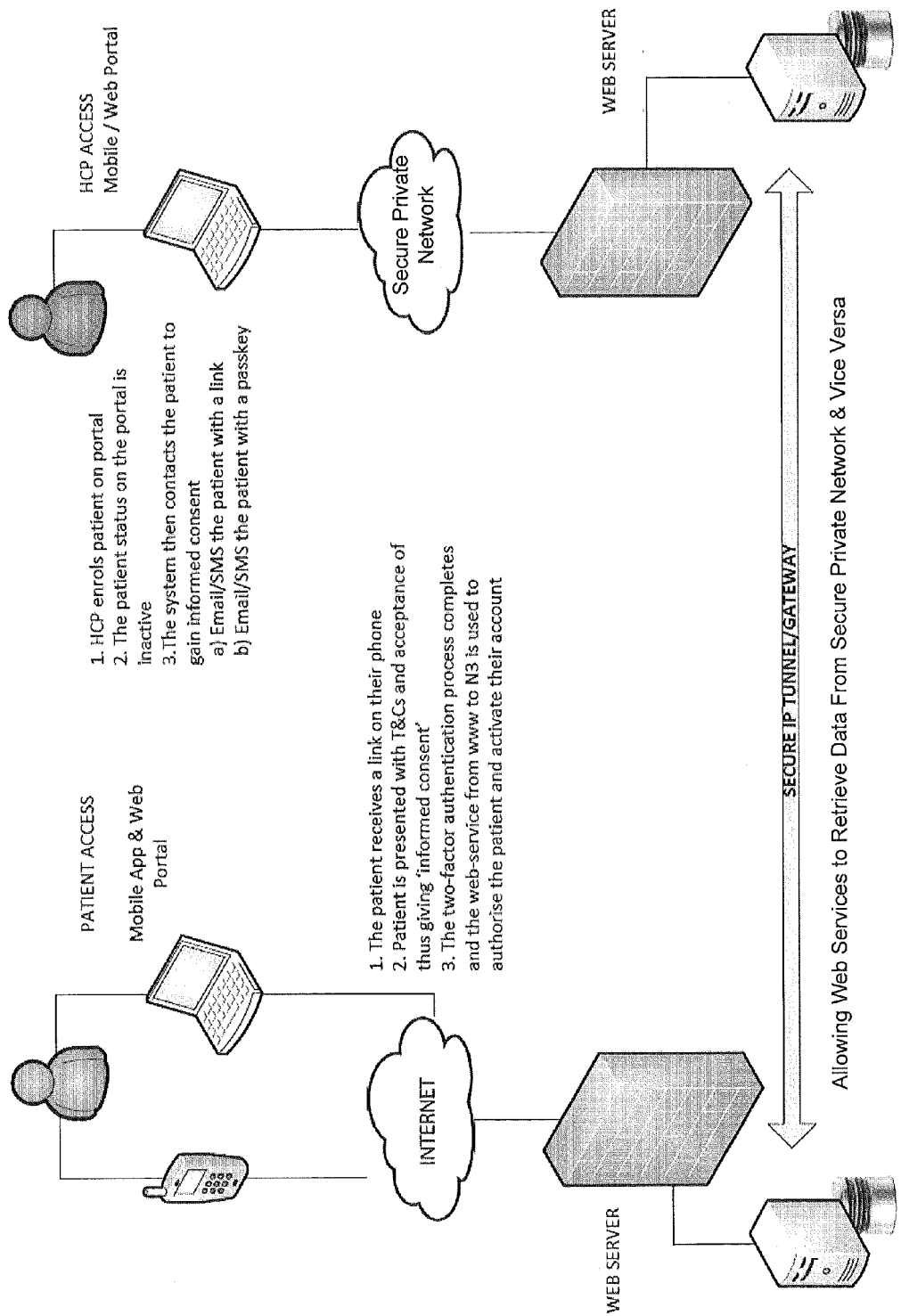
FIG. 12 is a flow diagram illustrating a high level architecture corresponding to systems, methods, solutions and computer program products according to some embodiments of the present invention.

Brief reference is now made to FIG. 12, which is a flow diagram illustrating a high level architecture corresponding to systems, methods, solutions and computer program products according to some embodiments of the present invention, Specifically, FIG. 12 may be representative of the distinction between the aggregate dataspace 506 and the individual dataspace 508 as discussed above regarding FIG. 9. For example, illustrated is the separation of the personally identifiable information (PII) (inside a secure health service network) and other systems and/or databases.

In some embodiments, the solution may be configured in a way to ensure the logical separation of personal identifiable information from other modules within the platform. Personal identifiers also known as PIDs are a subset of PII data elements that may identify a unique individual and may permit another person to "assume" that individual's identity without their knowledge or consent.

Some embodiments provide that security elements applied in the platform include two factor authentication, emails, in-App notification, MMS, Instant Message and/or SMS messages, among others. In some embodiments, the patient may be enrolled onto the program/study by a health care professional. The health care professional may either retrieve the patient's details from an external system and re-enter those details via a system portal or an interface to a primary/secondary care system may provide these details directly into a system database. The healthcare professional may be required to enter either an email or phone number (mobile or landline). Depending on these choices, a choice of two factor authentications can be provided depending on the patient's individual preference and/or needs. Some embodiments provide that a generalized option may be provided for a patient population.

Some embodiments provide that the patient, although enrolled, is inactive and may remain so until they receive a URL and a passkey. The URL and passkey may be sent in separate notification media such as emails, in-App notification, MMS, Instant Message and/or SMS messages, among others. To activate their account via the patient portal the patient may access the link and enter the passkey.

Some embodiments provide that voice may be used in the two factor authentication. For example, the patient, although enrolled, is inactive and may remain so until they access a particular URL, which may provide access to the patient portal where they may enter a valid username and/or passkey. In some embodiments, the URL and/or username may be printed by the healthcare professional and given to the patient. In this manner, upon access to the URL, the patient may be requested to enter a username. An automated voice call may be activated and may call the patient's landline number at which point they will be presented with a passkey to enter into the patient portal.

Some embodiments provide that the PII and/or the PID are logically separate from the other systems and may also be encrypted. In some embodiments, a foreign key which links the PII/PID to all the other systems may be provided by a technology that associates a device and a user that does so by storing this information separate from any other system, again provided a logical separation between PII/PID and the systems that may use their mobile and/or email contact information. During the activation process by the patient mDNA will determine what mobile device (or if it's a landline) they're using and will then generate what is known as an mDNA tag.

Some embodiments provide that any "touch-point" to patient data may be recorded which may provide audit trail data corresponding to any access, creation or change to patient data. This audit trail may contain data corresponding to the user that accessed, created and/or changed the data, a time stamp corresponding to this action and/or the action taken. The original data value may not be obscured by any change to the data value, thus allowing any and all changes to data to be traced back to the original data value. In some embodiments, the addition of a reason, rationale and/or justification for changing the data value may also be stored. Referencing FIG. 12, the main patient data may be presented via the health care professional portal, which will be within a secure private network that may only be accessed by health care professional and/or system service providers.

Various embodiments of the present invention are described below with reference to block diagrams illustrating methods, apparatus and computer program products according to various embodiments of the invention. It will be understood that each block of the block diagrams and/or operational illustrations, and combinations of blocks in the block diagrams and/or operational illustrations, can be implemented by analog and/or digital hardware, and/or computer program instructions. These computer program instructions may be provided to a processor of a general purpose computer, special purpose computer, ASIC, and/or other programmable data processing apparatus, such that the instructions, which execute via the processor of the computer and/or other programmable data processing apparatus, create means for implementing the functions/acts specified in the block diagrams and/or operational illustrations. Accordingly, it will be appreciated that the block diagrams and operational illustrations support apparatus, methods and computer program products.

In the drawings and specification, there have been disclosed typical embodiments of the invention and, although specific terms are employed, they are used in a generic and descriptive sense only and not for purposes of limitation, the scope of the invention being set forth in the following claims. Moreover, those skilled in the art will readily appreciate that many modifications are possible to the exemplary embodiments that are described in detail in the present specification that do not materially depart from the novel teachings and advantages of this invention. Accordingly, all such modifications are intended to be included within the scope of this invention as defined in the claims and equivalents thereof. The following claims are provided to ensure that the present application meets all statutory requirements as a priority application in all jurisdictions and shall not be construed as setting forth the scope of the present invention.

That which is claimed is:
1. A method of providing health condition specific adaptive content, the method comprising:
  receiving health condition specific information into a computer implemented data repository;
  defining health condition specific application requirements corresponding to the health condition specific information;

building a health condition specific application based on the requirements;

configuring the health condition specific application corresponding to user-specific attributes; and sending the health condition specific application to a patient mobile terminal used by a patient being treated for the condition that is operable to execute the health condition specific application by assessing a plurality of capabilities corresponding to the patient mobile terminal and at least one peripheral device attached thereto, wherein the patient mobile terminal is configured to receive and execute the health condition specific application that is configured by the at least one computer, and wherein building the health condition specific application based on the requirements, configuring the health condition specific application corresponding to user-specific attributes and delivering the health condition specific application to the patient mobile terminal are performed using one or more computers.

2. The method according to claim 1, wherein receiving the health condition specific information comprises receiving health condition related data.

3. The method according to claim 1, wherein receiving the health condition specific information comprises receiving disease specific data.

4. The method according to claim 1, wherein defining requirements corresponding to the health condition specific information comprises:

selecting a disease;

selecting at least one disease attribute of a plurality of disease attributes; and selecting at least one disease functional component of the condition specific application corresponding to the selected at least one disease attribute.

5. The method according to claim 1, wherein building the health condition specific application comprises:

defining function metadata corresponding to at least one functional component of the health condition specific application;

defining at least one function element based on the function metadata; and defining a function interface that corresponds to the at least one functional component of the health condition specific application.

6. The method according to claim 1, wherein configuring the health condition specific application corresponding to user-specific attributes comprises:

defining general rules and/or workflow corresponding to the condition specific application;

configuring a plurality of health condition stages that are specific to the condition;

mapping a plurality of behavior stages of the user that correspond to ones of the plurality of health condition stages; and mapping knowledgebase content to the plurality of health condition stages and/or the plurality of behavior stages.

7. The method according to claim 1, wherein delivering the health condition specific application to the patient mobile terminal that is operable to execute the health condition specific application comprises:

assessing a plurality of capabilities corresponding to the user;

packaging the health condition specific application corresponding to the plurality of capabilities of the patient mobile terminal, the user and/or at least one peripheral device; and modifying the packaged health condition specific application to include user specific data.

8. The method according to claim 1, further comprising modifying at least one component and/or operating mode of the health condition specific application responsive to a change in the health condition and/or user behavior.

9. The method according to claim 1, wherein the plurality of capabilities corresponding to the patient mobile terminal include an identification of one or more applications that are installed thereon.

10. The method according to claim 1, wherein the health condition specific information includes post diagnosis health condition specific information.

* * * * *